US008349798B2

(12) United States Patent
Sessa

(10) Patent No.: US 8,349,798 B2
(45) Date of Patent: *Jan. 8, 2013

(54) CAVEOLIN PEPTIDES AND THEIR USE AS THERAPEUTICS

(75) Inventor: William C. Sessa, Madison, CT (US)

(73) Assignee: Yale University, New Haven, CT (US)

( * ) Notice: Subject to any disclaimer, the term of this patent is extended or adjusted under 35 U.S.C. 154(b) by 1351 days.

This patent is subject to a terminal disclaimer.

(21) Appl. No.: 11/978,770

(22) Filed: Oct. 30, 2007

(65) Prior Publication Data

US 2012/0149651 A1 Jun. 14, 2012

Related U.S. Application Data

(60) Continuation of application No. 10/358,365, filed on Feb. 4, 2003, now Pat. No. 7,494,976, which is a division of application No. 09/731,023, filed on Dec. 7, 2000, now abandoned.

(60) Provisional application No. 60/231,327, filed on Sep. 8, 2000.

(51) Int. Cl.
*A61K 38/00* (2006.01)

(52) U.S. Cl. .......................................... 514/12; 530/324

(58) Field of Classification Search ........................ None
See application file for complete search history.

(56) References Cited

U.S. PATENT DOCUMENTS 6,261,760 B1 * 7/2001 Fielding et al. .................... 435/4

FOREIGN PATENT DOCUMENTS

EP 1 076 091 A1 2/2001

OTHER PUBLICATIONS

Michel et al (J of Biological Chemistry, 1997, 272:25907-25912, IDS).*
Garcia-Cardena et al (J Biological Chemistry, 1997, 272:25437-25440, IDS).*
Bucci, et al., In vivo delivery of the caveolin-1 scaffolding domain inhibits nitric oxide synthesis and reduces inflammation, *Nat. Med.* 6:1362-1367, 2000.
Couet, et al., Identification of peptide and protein ligands for the caveolin-scaffolding domain, *J. Biol. Chem.*, 272:6525-6533, 1997.
Derossi, et al., 1998, *Cell Biology*, 8:84-87.
Derossi, et al., Cell Internalization of the third helix of the Antennapedia homeodomain is receptor-independent, *J. Biol., Chem.*, 271:18188-18193, 1996.
Fawell, et al., Tat-mediated delivery of heterologous proteins into cells, *Proc. Natl. Acad. Sci. USA*, 91:664-668 (1994).
Feron, et al., Modulation of the endothelial nitric-oxide synthase-caveolin interaction in cardiac myocytes, *J. Biol. Chem.*, 273:30249-30254 (1998).
Garcia-Cardena, et al., Dissecting the interaction between nitric oxide synthase (NOS) and caveolin, *J. Biol. Chem.*, 272:25437-25440 (1997).
Garcia-Cardena, et al., Targeting of nitiric oxide synthase to endothelial cell caveolae via palmitoylation: implications for nitric oxide signaling, *Proc. Natl. Acad. Sci. USA*, 93:6448-6453 (1996).
Ghosh, et al., Interaction between caveolin-1 and the reductase domain of endothelial nitric-oxide synthase, *J. Biol. Chem.*, 273:22267-22271 (1998).

Guillermo, et al., 1997, *The Journal of Biological Chemistry*, 272:25437-25440.
Huang, et al., Hypertension in mice lacking the gene for endothelial nitric oxide synthase, *Nature*, 377:239-242 (1995).
Ju, et al., Direct interaction f endothelial nitric-oxide synthase and caveolin-1 inhibits synthase activity, *J. Biol. Chem.* 272:18522-18525 (1997).
Kurzchalia, et al., Membrane microdomains and caveolae, *Curr. Opin. Cell. Biol.*, 11:424-431 (1999).
Lee, et al., Impaired wound healing and angiogenesis in eNOS-deficient mice, *Am. J. Physiol.*, 277:H1600-1608 (1999).
Li, et al., Src tyrosine kinases, $G_2$ subunits, and H-Ras share a common membrane-anchored scaffolding proteing, caveolin, *J. Biol. Chem.*, 272:29182-29190 (1996).
Lin, eta l., Inhibition of nuclear translocation of transcription factor Nf-κB by a synthetic peptide containing a cell membrane-permeable motif and nuclear localization sequence, *J. Biol. Chem.*, 270:14255-14258 (1995).
Liu, et al., 1999, *The Journal of Biological Chemistry*, 274:15781-15785.
Liu, et al., The first 35 amino acids and fatty acylation sites determine the molecular targeting of endothelial nitric oxide synthase into a goigi region of cells: a green fluorescent protein study, *J. Cell. Biol.*, 137:1525-1535, 1997.
Mashimo, et al., 1999, *American Journal of Physiology*, 277:G745-G750.
Michel, et al., Caveolin versus calmodulin, *J. Biol. Chem.*, 272:25907-25912 (1997).
Murohara, et al., Nitric oxide synthase modulates angiogenesis in response to tissue ischemia, *J. Clin. Invest.*, 101:2567-2578, 1998.
Nasu, et al., Suppression of caveolin expression induces androgen sensitivity in metastatic androgen-insensitive mouse prostate cancer cells, *Nat. Med.*, 4:1062-1064 (1998).
Oehlke, Et al., Cellular update of an α-helical amphipathic model peptide with the potential to deliver polar compounds into the cell interior non-endocytically, *Biochim. Biophys. Acta*, 1414:127-139 (1998).
Razani, et al., Regulation of cAMP-mediated signal transduction via interaction of caveolins with the catalytic subunit of protein kinase A, *J. Biol. Chem.*, 24:26353-26360 (1999).
Rojas, et al., Controlling epidermal growth factor (EGF)-stimulated Ras activation in intact cells by a cell-permeable peptide mimicking phosphorylated EGF receptor, *J. Biol. Chem.*, 271:27456-27461 (1996).
Roy, et al., Dominant-negative caveolin inhibits H-Ras function by disrupting cholesterol-rich plasma membrane domains, *Nat. Cell Biol.*, 1:98-105 (1999).
Rudic, et al., Direct evidence for the importance of endothelium-derived nitric oxide in vascular remodeling, *J. Clin. Invest.*, 101:731-736 (1998).
Smart, et al., 1999, *Molecular and Cellular Biology*, 19:7289-7304.
Smart, et al., Caveloins, liquid-ordered domains, and signal transduction, *Mol. Cell. Biol.*, 19:7289-7304 (1999)
Sternberg, et al., Caveolin, cholesterol and Ras signaling, *Nat. Cell Biol.*, 1:E35-37 (1999).

* cited by examiner

*Primary Examiner* — Laura B Goddard
(74) *Attorney, Agent, or Firm* — Riverside Law LLP

(57) ABSTRACT

The present invention relates generally to compositions and methods useful for treating various conditions and afflictions, such as inflammation and cancer. More specifically, the present invention relates to compositions and methods of treatment which utilize peptides comprising at least one caveolin scaffolding domain. Even more specifically, the present invention relates to compositions of fusion peptides comprising the antennapedia homeodomain fused to a caveolin scaffolding domain and to methods of using these peptides to treat various conditions and afflictions.

6 Claims, 10 Drawing Sheets

A

B

A

B

SEQUENCE LISTING

<160> NUMBER OF SEQ ID NOS: 12

<210> SEQ ID NO 1
<211> LENGTH: 20
<212> TYPE: PRT
<213> ORGANISM: Homo sapiens
<220> FEATURE:
<223> OTHER INFORMATION: Amino acids 82-101 of human caveolin-1

<400> SEQUENCE: 1

Asp Gly Ile Trp Lys Ala Ser Phe Thr Thr Phe Thr Val Thr Lys Tyr
 1               5                  10                  15

Trp Phe Tyr Arg
            20

<210> SEQ ID NO 2
<211> LENGTH: 44
<212> TYPE: PRT
<213> ORGANISM: Homo sapiens
<220> FEATURE:
<223> OTHER INFORMATION: Amino acids 135-178 of human caveolin-1

<400> SEQUENCE: 2

Lys Ser Phe Leu Ile Glu Ile Gln Cys Thr Ser Arg Val Tyr Ser Ile
 1               5                  10                  15

Tyr Val His Thr Val Cys Asp Pro Leu Phe Glu Ala Val Gly Lys Ile
            20                  25                  30

Phe Ser Asn Val Arg Ile Asn Leu Gln Leu Glu Ile
        35                  40

<210> SEQ ID NO 3
<211> LENGTH: 20
<212> TYPE: PRT
<213> ORGANISM: Rattus norvegicus
<220> FEATURE:
<223> OTHER INFORMATION: Amino acids 55-74 of rat caveolin-3

<400> SEQUENCE: 3

Asp Gly Val Trp Arg Val Ser Tyr Thr Thr Phe Thr Val Thr Lys Tyr
 1               5                  10                  15

Trp Cys Tyr Arg
            20

<210> SEQ ID NO 4
<211> LENGTH: 22
<212> TYPE: PRT
<213> ORGANISM: Rattus norvegicus
<220> FEATURE:
<223> OTHER INFORMATION: Amino acids 108-129 of rat caveolin-3

<400> SEQUENCE: 4

Lys Ser Tyr Leu Ile Glu Ile Gln Cys Ile Ser His Ile Tyr Ser Leu
 1               5                  10                  15

Cys Ile Arg Thr Phe Cys
            20

<210> SEQ ID NO 5
<211> LENGTH: 838
<212> TYPE: DNA
<213> ORGANISM: Homo sapiens
<220> FEATURE:
<221> NAME/KEY: CDS
<222> LOCATION: (35)..(568)
<223> OTHER INFORMATION: Human caveolin-1

```
<220> FEATURE:
<221> NAME/KEY: variation
<222> LOCATION: (278)
<223> OTHER INFORMATION: s = c or g; Xaa (amino acid 82) = His or Asp.

<400> SEQUENCE: 5
gaattccgga gttttcatcc agccacgggc cagc atg tct ggg ggc aaa tac gta      55
                                     Met Ser Gly Gly Lys Tyr Val
                                      1               5 gac tcg gag gga cat ctc tac acc gtt ccc atc cgg gaa cag ggc aac      103
Asp Ser Glu Gly His Leu Tyr Thr Val Pro Ile Arg Glu Gln Gly Asn
            10                  15                  20 atc tac aag ccc aac aac aag gcc atg gca gac gag ctg agc gag aag      151
Ile Tyr Lys Pro Asn Asn Lys Ala Met Ala Asp Glu Leu Ser Glu Lys
        25                  30                  35 caa gtg tac gac gcg cac acc aag gag atc gac ctg gtc aac cgc gac      199
Gln Val Tyr Asp Ala His Thr Lys Glu Ile Asp Leu Val Asn Arg Asp
 40              45                  50                  55 cct aaa cac ctc aac gat gac gtg gtc aag att gac ttt gaa gat gtg      247
Pro Lys His Leu Asn Asp Asp Val Val Lys Ile Asp Phe Glu Asp Val
                60                  65                  70 att gca gaa cca gaa ggg aca cac agt ttt sac ggc att tgg aag gcc      295
Ile Ala Glu Pro Glu Gly Thr His Ser Phe Xaa Gly Ile Trp Lys Ala
            75                  80                  85 agc ttc acc acc ttc act gtg acg aaa tac tgg ttt tac cgc ttg ctg      343
Ser Phe Thr Thr Phe Thr Val Thr Lys Tyr Trp Phe Tyr Arg Leu Leu
        90                  95                 100 tct gcc ctc ttt ggc atc ccg atg gca ctc atc tgg ggc att tac ttc      391
Ser Ala Leu Phe Gly Ile Pro Met Ala Leu Ile Trp Gly Ile Tyr Phe
    105                 110                 115 gcc att ctc tct ttc ctg cac atc tgg gca gtt gta cca tgc att aag      439
Ala Ile Leu Ser Phe Leu His Ile Trp Ala Val Val Pro Cys Ile Lys
120                 125                 130                 135 agc ttc ctg att gag att cag tgc acc agc cgt gtc tat tcc atc tac      487
Ser Phe Leu Ile Glu Ile Gln Cys Thr Ser Arg Val Tyr Ser Ile Tyr
                140                 145                 150 gtc cac acc gtc tgt gac cca ctc ttt gaa gct gtt ggg aaa ata ttc      535
Val His Thr Val Cys Asp Pro Leu Phe Glu Ala Val Gly Lys Ile Phe
                155                 160                 165 agc aat gtc cgc atc aac ttg cag aaa gaa ata taaatgacat ttcaaggata    588
Ser Asn Val Arg Ile Asn Leu Gln Lys Glu Ile
        170                 175 gaagtatacc tgattttttt tcctttttaat tttcctggtg ccaatttcaa gttccaagtt   648
gctaatacag caacgaattt atgaattgaa ttatcttggt tgaaaataaa aagatcactt    708
tctcagtttt cataagtatt atgtctcttc tgagctattt catctatttt tggcagtctg    768 aattttttaaa acccatttat atttctttcc ttacctttt atttgcatgt ggatcaacca    828
tcgctttatt                                                           838

<210> SEQ ID NO 6
<211> LENGTH: 178
<212> TYPE: PRT
<213> ORGANISM: Homo sapiens
<220> FEATURE:
<221> NAME/KEY: variation
<222> LOCATION: (82)
<223> OTHER INFORMATION: Xaa (amino acid 82) = His or Asp.

<400> SEQUENCE: 6

Met Ser Gly Gly Lys Tyr Val Asp Ser Glu Gly His Leu Tyr Thr Val
 1               5                  10                  15
```

```
Pro Ile Arg Glu Gln Gly Asn Ile Tyr Lys Pro Asn Asn Lys Ala Met
            20                  25                  30

Ala Asp Glu Leu Ser Glu Lys Gln Val Tyr Asp Ala His Thr Lys Glu
        35                  40                  45

Ile Asp Leu Val Asn Arg Asp Pro Lys His Leu Asn Asp Asp Val Val
 50                  55                  60

Lys Ile Asp Phe Glu Asp Val Ile Ala Glu Pro Glu Gly Thr His Ser
 65                  70                  75                  80

Phe Xaa Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
            100                 105                 110

Leu Ile Trp Gly Ile Tyr Phe Ala Ile Leu Ser Phe Leu His Ile Trp
            115                 120                 125

Ala Val Val Pro Cys Ile Lys Ser Phe Leu Ile Glu Ile Gln Cys Thr
        130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile

<210> SEQ ID NO 7
<211> LENGTH: 613
<212> TYPE: DNA
<213> ORGANISM: Rattus norvegicus
<220> FEATURE:
<221> NAME/KEY: CDS
<222> LOCATION: (134)..(586)
<223> OTHER INFORMATION: Rat caveolin-3

<400> SEQUENCE: 7
atgctgggtg gggcctattt agccggcagg ggcaccagtc tggagaccct aagcttggtc      60
tttctgcccc aggactgtca acaataccag ccacaagatt ctgatctcct cccgaaggtg     120
ccccagcctc aca atg atg acc gaa gag cac aca gat ctg gag gca cgg       169
              Met Met Thr Glu Glu His Thr Asp Leu Glu Ala Arg
                1               5                   10 atc atc aag gac att cac tgc aag gag ata gac ttg gtg aac aga gac      217
Ile Ile Lys Asp Ile His Cys Lys Glu Ile Asp Leu Val Asn Arg Asp
            15                  20                  25 ccc aag aac atc aat gag gac att gtg aag gtg gat ttt gaa gat gtg      265
Pro Lys Asn Ile Asn Glu Asp Ile Val Lys Val Asp Phe Glu Asp Val
 30                  35                  40 att gcg gag ccc gag ggc act tac agc ttc gat ggc gtg tgg agg gtg      313
Ile Ala Glu Pro Glu Gly Thr Tyr Ser Phe Asp Gly Val Trp Arg Val
 45                  50                  55                  60 agc tac acc act ttc acc gtc tcc aag tac tgg tgc tac cgc ctg ctg      361
Ser Tyr Thr Thr Phe Thr Val Ser Lys Tyr Trp Cys Tyr Arg Leu Leu
                65                  70                  75 tct aca ctg ctg ggt gtt cca ctg gcc ctg ctc tgg gga ttc ctg ttt      409
Ser Thr Leu Leu Gly Val Pro Leu Ala Leu Leu Trp Gly Phe Leu Phe
            80                  85                  90 gcc tgt atc tcc ttc tgc cac atc tgg gcc gtg gtg ccc tgc att aag      457
Ala Cys Ile Ser Phe Cys His Ile Trp Ala Val Val Pro Cys Ile Lys
        95                  100                 105 agc tac ctg att gag atc cag tgc atc agc cac atc tac tca ctg tgt      505
Ser Tyr Leu Ile Glu Ile Gln Cys Ile Ser His Ile Tyr Ser Leu Cys
110                 115                 120
```

-continued

```
atc cgc acc ttc tgc aac ccg ctc ttt gcc gca ctg ggc cag gtc tgc    553
Ile Arg Thr Phe Cys Asn Pro Leu Phe Ala Ala Leu Gly Gln Val Cys
125             130                 135                 140 agc aac att aag gtg gtg ctg cga agg gaa ggc taactgtggg gaaggctggg   606
Ser Asn Ile Lys Val Val Leu Arg Arg Glu Gly
                145                 150 caggggg                                                             613
```

<210> SEQ ID NO 8
<211> LENGTH: 151
<212> TYPE: PRT
<213> ORGANISM: Rattus norvegicus

<400> SEQUENCE: 8

```
Met Met Thr Glu Glu His Thr Asp Leu Glu Ala Arg Ile Ile Lys Asp
 1               5                  10                  15

Ile His Cys Lys Glu Ile Asp Leu Val Asn Arg Asp Pro Lys Asn Ile
             20                  25                  30

Asn Glu Asp Ile Val Lys Val Asp Phe Glu Asp Val Ile Ala Glu Pro
         35                  40                  45

Glu Gly Thr Tyr Ser Phe Asp Gly Val Trp Arg Val Ser Tyr Thr Thr
     50                  55                  60

Phe Thr Val Ser Lys Tyr Trp Cys Tyr Arg Leu Leu Ser Thr Leu Leu
 65                  70                  75                  80

Gly Val Pro Leu Ala Leu Leu Trp Gly Phe Leu Phe Ala Cys Ile Ser
                 85                  90                  95

Phe Cys His Ile Trp Ala Val Val Pro Cys Ile Lys Ser Tyr Leu Ile
            100                 105                 110

Glu Ile Gln Cys Ile Ser His Ile Tyr Ser Leu Cys Ile Arg Thr Phe
        115                 120                 125

Cys Asn Pro Leu Phe Ala Ala Leu Gly Gln Val Cys Ser Asn Ile Lys
    130                 135                 140

Val Val Leu Arg Arg Glu Gly
145                 150
```

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Scrambled control peptide Cav-X

<400> SEQUENCE: 9

```
Trp Gly Ile Asp Lys Ala Phe Phe Thr Thr Ser Thr Val Thr Tyr Lys
 1               5                  10                  15

Trp Phe Arg Tyr
            20
```

<210> SEQ ID NO 10
<211> LENGTH: 16
<212> TYPE: PRT
<213> ORGANISM: Drosophila melanogaster
<220> FEATURE:
<221> NAME/KEY: DOMAIN
<222> LOCATION: (1)..(16)
<223> OTHER INFORMATION: Homeodomain, internalization sequence

<400> SEQUENCE: 10

```
Arg Gln Ile Lys Ile Trp Phe Gln Asn Arg Arg Met Lys Trp Lys Lys
 1               5                  10                  15
```

```
<210> SEQ ID NO 11
<211> LENGTH: 36
<212> TYPE: PRT
<213> ORGANISM: Artificial Sequence
<220> FEATURE:
<223> OTHER INFORMATION: Description of Artificial Sequence:
      Antennapedia-caveolin-1 scaffolding domain fusion
      peptide

<400> SEQUENCE: 11

Arg Gln Ile Lys Ile Trp Phe Gln Asn Arg Arg Met Lys Trp Lys Lys
 1               5                  10                  15

Asp Gly Ile Trp Lys Ala Ser Phe Thr Thr Phe Thr Val Thr Lys Tyr
             20                  25                  30

Trp Phe Tyr Arg
         35

<210> SEQ ID NO 12
<211> LENGTH: 36
<212> TYPE: PRT
<213> ORGANISM: Artificial Sequence
<220> FEATURE:
<223> OTHER INFORMATION: Description of Artificial Sequence:
      Antennapedia-cav-X fusion peptide

<400> SEQUENCE: 12

Arg Gln Ile Lys Ile Trp Phe Gln Asn Arg Arg Met Lys Trp Lys Lys
 1               5                  10                  15

Trp Gly Ile Asp Lys Ala Phe Phe Thr Thr Ser Thr Val Thr Tyr Lys
             20                  25                  30

Trp Phe Arg Tyr
         35
```

CAVEOLIN PEPTIDES AND THEIR USE AS THERAPEUTICS

CROSS REFERENCE TO RELATED APPLICATION

This Application is a continuation of U.S. application Ser. No. 10/358,365, filed Feb. 4, 2003, which is a divisional application of Ser. No. 09/731,023, filed Dec. 7, 2000, which is entitled to a claim of priority under 35 U.S.C. §119(e) to U.S. Provisional Patent Application No. 60/231,327, filed Sep. 8, 2000.

U.S. GOVERNMENT SUPPORT

This work was supported by grants from the National Institute of Health (HL61371; HL64793).

FIELD OF THE INVENTION

The present invention relates generally to compositions and methods useful for treating various conditions and afflictions, such as inflammation and cancer. More specifically, the present invention relates to compositions and methods of treatment which utilize peptides comprising at least one caveolin scaffolding domain. Even more specifically, the present invention relates to compositions of fusion peptides comprising the antennapedia homeodomain fused to a caveolin scaffolding domain and to methods of using these peptides to treat various conditions and afflictions.

BACKGROUND OF THE INVENTION

Caveolins are cholesterol binding proteins that can potentially regulate a variety of signal transduction pathways (Smart et al., (1999) Mol. Cell. Biol. 19, 7289-7304; Kurzchalia & Parton, (1999) Curr. Opin. Cell. Biol. 11, 424-431). For example, numerous researchers have demonstrated localization of proteins in caveolae, interaction of these proteins with caveolins, and the ability of overexpressed caveolins or peptides derived from caveolins to suppress or stimulate signaling functions in vitro or in cultured cells (Li et al., (1996) J. Biol. Chem. 271, 29182-29190; Razani et al., (1999) J. Biol. Chem. 274, 26353-26360; Nasu et al., (1998) Nat. Med. 4, 1062-1064; Garcia-Cardena et al., (1997) J. Biol. Chem. 272, 25437-25440). However, the importance of caveolins as modulators of signal transduction in vivo is controversial since caveolins-1 and -3, per se, are cholesterol binding proteins that deliver cholesterol from the endoplasmic reticulum to the plasmalemma thereby regulating signal transduction indirectly by modulating the cholesterol content of lipid raft domains and caveolae (Roy et al., (1999) Nat. Cell Biol. 1, 98-105; Sternberg et al., (1999) Nat. Cell Biol. 1, E35-37).

Recent studies have focused on the subcellular trafficking and regulation of endothelial nitric oxide synthase (eNOS). eNOS derived NO is necessary for the maintenance of systemic blood pressure, vascular remodeling, angiogenesis and wound healing (Huang et al., (1995) Nature 377, 239-242; Murohara et al., (1998) J. Clin. Invest. 101, 2567-0.2578; Rudic et al., (1998) J. Clin. Invest. 101, 731-736; Lee et al., (1999) Am. J. Physiol. 277, H1600-1608). eNOS is a dually acylated, peripheral membrane protein that targets to lipid raft domains and caveolae (Garcia-Cardena et al., (1996) Proc. Natl. Acad. Sci. USA 93, 6448-6453; Liu et al., (1997) J. Cell Biol. 137, 1525-1535). In caveolae, eNOS can physically interact with caveolins-1 and -3 by binding to their putative scaffolding domain located between amino acids 82-101 (Li et al., (1996) J. Biol. Chem. 271, 29182-29190) and this interaction, renders eNOS in its "less active" state (Garcia-Cardena et al., (1997) J. Biol. Chem. 272, 25437-25440; Ju et al., (1997) J. Biol. Chem. 272, 18522-18525; Michel et al., (1997) J. Biol. Chem. 272, 25907-25912). The data for this model was largely elucidated in vitro either using overexpression systems, fusion proteins or yeast-two hybrid screening to map the interacting domains.

In support of caveolin as a negative regulator of eNOS are studies showing that peptides derived from the scaffolding domain of caveolin-1 will disrupt the binding of eNOS to caveolin and dose-dependently inhibit NOS activity in vitro ($IC_{50}$=1-3 µM) by slowing electron flux from the reductase to the oxygenase domain of NOS (Garcia-Cardena et al., (1997) J. Biol. Chem. 272, 25437-25440; Ju et al., (1997) J. Biol. Chem. 272, 18522-18525; Ghosh et al., (1998) J. Biol. Chem. 273, 22267-22271).

The present invention demonstrates that the treatment of one or more cells with a peptide comprising at least one caveolin scaffolding domain results in the reduction and/or elimination of one or more conditions or afflictions of the treated tissue, organ or organism. For example, treatment with a peptide comprising at least one caveolin scaffolding domain results in the reduction or elimination of inflammation and tumor cell angiogenesis and proliferation.

The present invention also demonstrates the use of antennapedia fusion peptides ("AP fusions") to deliver bioactive peptides to cells of the vasculature in vitro and in vivo. Previous work utilizing this method of delivery has focused on the fusion of AP with oligonucleotides and small peptides for treatment of cells in culture. The uptake of AP bound cargo into cells is rapid, independent of membrane fluidity and is not affected by extremes in temperature (Derossi et al., (1996) J. Biol. Chem. 271, 18188-18193).

In the present experiments, Caveolin-1 scaffolding domain—antennapedia fusion peptides ("AP-Cav") either in their biotinylated or rhodamine labeled forms, were internalized by the endothelium. Moreover, based on the anti-inflammatory actions of AP-Cav in vivo, the fusion peptides must be stable enough to survive first pass metabolism in the liver and pulmonary circuit to deliver the active peptides to the sites of inflammation. Preliminary evidence indicates that the AP-Cav peptides of the present invention do not increase blood pressure when delivered in vivo. Thus, the compositions and methods of the present invention provide useful approaches to delivering anti-sense oligonucleotides or as part of viral delivery systems for therapeutic cardiovascular gene targeting in vivo.

While not wishing to be bound by any particular theory, the fusion peptides of the present invention appear to be blocking one or more proteins that interact with or have the potential to interact with caveolin. Examples of such caveolin bound proteins include, but are not limited to, eNOS, the "Src Family" of tyrosine kinases (e.g., Src, Fyn, Lck, Yes, Lyn, Blk, Hick, Fgr, Yrk), Scr-like kinases, Ras proteins (e.g., Rho, Rac, Rab), Raf proteins (e.g., Raf-1, A-Raf, B-Raf), EGF receptors, and MAP kinases (e.g., Fus3) (Couet al. (1997) J. Biol. Chem. 272, 6525-6533; Lewin (2000) Genes vii, Signal Transduction, pp. 801-834, Oxford University Press; Smith et al. (1997) Oxford Dictionary of Biochemistry & Molecular Biology, Oxford University Press).

SUMMARY OF THE INVENTION

This invention provides methods for blocking the interaction of a caveolin with a protein in vivo wherein the method comprises administering an effective amount of a peptide which comprises a caveolin scaffolding domain. More specifically, this invention provides such methods wherein the interaction comprises the binding of a protein to a caveolin.

This invention also provides methods for the down regulating a caveolin-binding protein in vivo wherein the method comprises administering an effective amount of a peptide which comprises a caveolin scaffolding domain.

This invention further provides methods for inhibiting inflammation in an animal wherein the method comprises administering an effective amount of a peptide which comprises a caveolin scaffolding domain.

This method also provides methods for inhibiting tumor cell angiogenesis and proliferation in an animal wherein the method comprises administering an effective amount of a peptide which comprises a caveolin scaffolding domain.

This invention provides each of the aforementioned methods wherein the caveolin scaffolding domain is selected from the group consisting of SEQ ID NO: 1, SEQ ID NO: 2, SEQ ID NO: 3 and SEQ ID NO: 4. In addition, this invention provides such methods wherein the peptide further comprises a membrane translocation domain. More specifically, this invention provides such methods wherein the membrane translocation domain comprises the third helix of the antennapedia homeodomain. Even more specifically, this invention provides such methods wherein the membrane translocation domain has the sequence provided in SEQ ID NO: 10. An exemplary target protein in such methods is the eNOS. A specific example of a fusion peptide useful in this invention is that provided in SEQ ID NO: 11.

This invention provides fusion peptides comprising at least one caveolin scaffolding domain and at least one membrane translocation domain. Examples of caveolin scaffolding domains useful in this invention include, but are not limited to, those selected from the group consisting of SEQ ID NO: 1, SEQ ID NO: 2, SEQ ID NO: 3 and SEQ ID NO: 4. In addition, this invention provides fusion peptides wherein the membrane translocation domain facilitates membrane translocation in vivo. More specifically, this invention provides such fusion peptides wherein the membrane translocation domain comprises the third helix of the antennapedia homeodomain. Even more specifically, this invention provides fusion peptides which have the sequence provided in SEQ ID NO: 11.

This invention provides isolated peptides including (a) isolated peptides comprising an amino acid sequence selected from the group consisting of SEQ ID NO: 1, SEQ ID NO: 2, SEQ ID NO: 3 and SEQ ID NO: 4; (b) isolated peptides comprising a fragment of at least three amino acids of an amino acid sequence selected from the group consisting of SEQ ID NO: 1, SEQ ID NO: 2, SEQ ID NO: 3 and SEQ ID NO: 4; (c) isolated peptides comprising conservative amino acid substitutions of the amino acid sequences selected from the group consisting of SEQ ID NO: 1, SEQ ID NO: 2, SEQ ID NO: 3 and SEQ ID NO: 4; and (d) naturally occurring amino acid sequence variants of amino acid sequences selected from the group consisting of SEQ ID NO: 1, SEQ ID NO: 2, SEQ ID NO: 3 and SEQ ID NO: 4.

This invention further provides compositions which include the fusion peptides discussed herein. In addition, this invention provides such compositions which further include one or more carriers.

This invention also provides isolated peptides consisting of the amino acid sequences of SEQ ID NO: 1, SEQ ID NO: 2, SEQ ID NO: 3, SEQ ID NO: 4 or SEQ ID NO: 11.

This invention further provides methods for down-regulating eNOS activity in a cell comprising administering an effective amount of a peptide which down-regulates at least one activity of eNOS. More specifically, this invention provides such methods wherein the peptide comprises at least one caveolin scaffolding domain. Even more specifically, this invention provides such methods wherein the peptide further comprises at least one membrane translocation domain. Peptides useful in the methods of this invention include, but are not limited to, those provided in SEQ ID NO: 1, SEQ ID NO: 2, SEQ ID NO: 3 and SEQ ID NO: 4.

This invention provides methods of down-regulating eNOS activity wherein such activities include the synthesis and/or production of NO. Furthermore, the methods of this invention provides such methods wherein the down-regulation of eNOS activity results in blockade of vasodilation.

This invention provides methods of inhibiting inflammation in a mammal comprising administering an effective amount of a peptide which down-regulates at least one activity of eNOS.

This invention also provides methods of inhibiting tumor cell angiogenesis and proliferation in a mammal comprising administering an effective amount of a peptide which down-regulates at least one activity of eNOS. Furthermore, this invention provides such methods wherein the peptide is administered in combination with a chemotherapeutic agent.

This invention also provides methods of inhibiting eNOS-dependent vasodilation in a mammal comprising administering an effective amount of a peptide which down-regulates at least one activity of eNOS.

The present invention provides methods of identifying an agent which interacts with eNOS comprising: (a) exposing cells which express eNOS to an agent; and (b) determining if the agent binds to eNOS, thereby identifying an agent which interacts with eNOS.

The present invention further provides methods of identifying an agent which modulates at least one activity of eNOS comprising the steps of: (a) exposing cells which express eNOS to an agent; and (b) determining whether the agent modulates the activity of eNOS, thereby identifying an agent which modulates an activity of eNOS. The methods of the present invention are useful for modulating eNOS activities such as, but not limited to, acetycholine-induced vasodilation, prostacyclin production and NO production.

DETAILED DESCRIPTION

I. General Description

Figure 1:
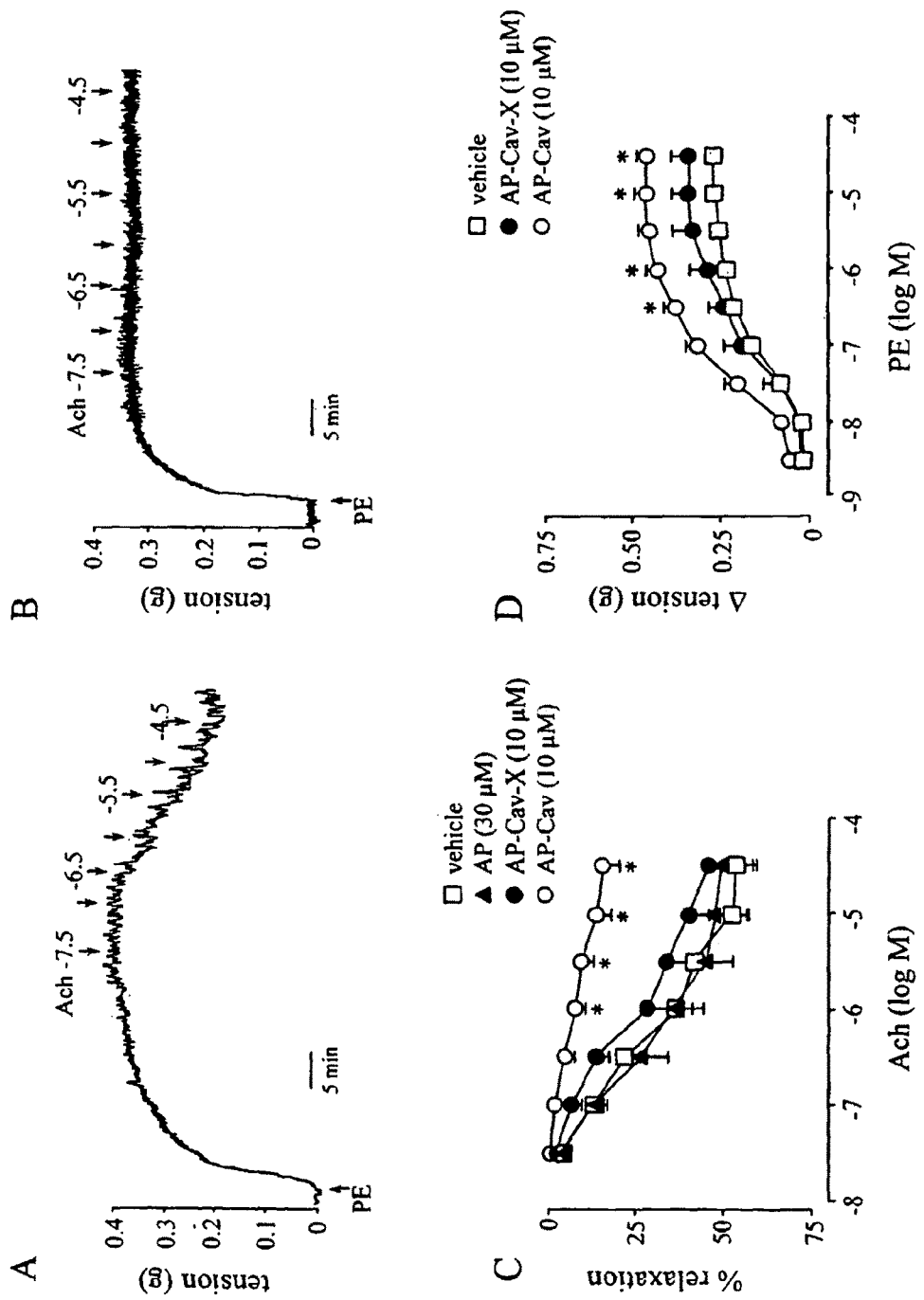
FIG. 1—Caveolin scaffolding domain peptide inhibits acetylcholine (Ach)-induced relaxation and potentiates phenylephrine-induced contraction of the isolated mouse aorta. Mouse aorta were incubated for twenty hours with either 10 μM AP-Cav-X (A) or AP-Cav (B) and mounted in organ bath chambers. Following phenylephrine (PE) precontraction, the vessels were subjected to increasing concentration of Ach (30 nM to 30 μM expressed as log molar concentration). (C) shows summary of the data presented in (A) and (B). Note that AP alone (30 μM) does not affect Ach induced relaxations. (D) shows the effect of 10 μM AP-Cav-X or AP-Cav peptides on phenylephrine concentration response curves in isolated mouse aortas (*$p<0.05$ compared to vehicle alone; n=6-8 rings per treatment).

The invention relates generally to compositions and methods for the selective inhibition of eNOS both in vitro and in vivo using fusion peptides comprising a membrane translocation sequence fused to a caveolin scaffolding domain sequence. The invention relates specifically to compositions of fusion peptides comprising the antennapedia homeodomain fused to the caveolin-1 scaffolding domain and methods of using these peptides. These methods include inhibition of in vivo physiological activity associated with eNOS such as inflammation and tumor cell angiogenesis and proliferation.

The invention also relates to in vivo methods for facilitating entry of a peptide into a cell by linking the peptide to a second distinct peptide comprising a membrane translocation domain.

The invention further includes methods for screening and identifying agents capable of interacting with eNOS thereby blocking the production of NO. The invention also includes the use of these agents in the treatment of disorders associated with regulation of NO production by eNOS.

II. Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, the term "binding" refers to the adherence of molecules to one another, such as, but not limited to, enzymes to substrates, antibodies to antigens, DNA strands to their complementary strands. Binding occurs because the shape and chemical nature of parts of the molecule surfaces are complementary. A common metaphor is the "lock-and-key" used to describe how enzymes fit around their substrate. The binding of the caveolin protein may occur at one or more domains of eNOS, such as, but not limited to, the oxygenase domain of eNOS and/or the reductase domain of eNOS.

As used herein, the term "fusion peptide" or "fusion polypeptide" or "fusion protein" or "fusion peptidomimetic" or "fusion non-peptide-analog" refers to a heterologous peptide, heterologous polypeptide, heterologous protein, peptidomimetic, or non-peptide analog linked to a membrane translocation domain.

As used herein, the terms "conservative variation" or "conservative substitution" as used herein refers to the replacement of an amino acid residue by another, biologically similar residue. Conservative variations or substitutions are not likely to change the shape of the peptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine, and the like.

As used herein, the term "caveolin scaffolding domain" refers to domains inclusive of putative scaffolding domains of any caveolin protein. Thus, the term as it used herein is not limited to putative scaffolding domains. Examples of caveolin scaffolding domains include, but are not limited to, the following:

(a) Amino acids 82-101 of human caveolin-1($^{82}$DGIWKASFTTFTVTKYWFYR$^{101}$) (SEQ ID NO: 1) or canine equivalents. The complete sequence of human Cav-1 can be found at GenBank Accession No. Z18951 and is provided in SEQ ID NO: 5.

(b) Amino acids 135-178 of human caveolin-1($^{135}$KSFLIEIQCTSRVYSIYVHTVCD-PLFEAVGKIFSNVRINLQLEI$^{178}$) (SEQ ID. NO: 2) or canine equivalents.

(c) Amino acids 55-74 of rat caveolin-3 ($^{65}$DGVWRVSYTTFTVTKYWCYR$^{84}$) (SEQ ID NO: 3) or human equivalents. The complete sequence for rat Cav-3 is provided in SEQ ID NO: 7. The complete sequence of human Cav-3 can be found at GenBank Accession No. AF036366.1; 39-152, 32-373. The complete protein code for human Cav-3 can be found at GenBank Accession No. AAC39758.1.

(d) Amino acids 108-129 of rat caveolin-3 ($^{109}$KSYLIEIQCISHFYSLCIRTFC$^{130}$) (SEQ ID NO: 4) or human equivalents.

As used herein, the term "domain" refers to a part of a molecule or structure that shares common physicochemical features, such as, but not limited to, hydrophobic, polar, globular and helical domains or properties. Specific examples of binding domains include, but are not limited to, DNA binding domains and ATP binding domains.

As used herein, the term "eNOS" or "endothelial Nitric Oxide Synthase" or "Nitric Oxide Synthase III" refers to an enzyme that catalyzes the conversion of L-arginine, NADPH, and oxygen to citrulline, nitric oxide, and NADP+ and is expressed in endothelial cells.

As used herein, the term "heterologous peptide" refers to any peptide, polypeptide or protein whose sequence is chosen in such a way that the product of the fusion of this sequence with the membrane translocation domain has a sequence different from the wild-type sequence flanking any membrane translocation domain.

As used herein, the term "membrane translocation domain" refers to a peptide capable of permeating the membrane of a cell and which is used to transport attached peptides into a cell in vivo. Membrane translocation domains include, but are not limited to, the third helix of the antennapedia homeodomain protein (Derossi et al., (1994) J. Biol. Chem. 269, 10444-10450; U.S. Pat. Nos. 5,888,762 & 6,015,787); Tat derived peptides (Fawell et al. (1994) Proc. Natl. Acad. Sci. 91, 664-668); alpha helical amphipathic peptides (Oehlke et al., (1998) Biochim. Biophys. Acta 1414, 127-139; and peptides referred to as SKP or SN50 (Lin et al. (1995) J. Biol. Chem. 270, 14255-14258) or SP1068 (Rojas et al. (1996) J. Biol. Chem. 271, 27456-27461).

As used herein, the term "wild-type" refers to the genotype and phenotype that is characteristic of most of the members of a species occurring naturally and contrasting with the genotype and phenotype of a mutant.

II. Specific Embodiments

A. Agents which Interact with eNOS

The identification of the interaction of the caveolin scaffolding domain with eNOS allows for the discovery of compounds that are capable of down-regulating the activity of eNOS, for example, modulating its production of nitric oxide (NO). Binding of caveolins to eNOS results in decreased production of NO by eNOS. Molecules that down-regulate eNOS-dependent production of NO are therefore part of the invention. Down-regulation is defined here as a decrease in activation, function or synthesis of NO. It is further defined to include an increase in the degradation of the eNOS gene, its protein product, ligands or activators. Down-regulation is therefore achieved in a number of ways. For example, administration of molecules that can stabilize the binding of caveolins to eNOS. Such molecules encompass peptide products, including those encoded by the DNA sequences of caveolin-1 or DNA sequences containing various mutations. These mutations may be point mutations, insertions, deletions or spliced variants of any caveolin gene encoding the caveolin scaffolding domain. This invention also includes truncated peptides encoded by the DNA molecules described above. These peptides being capable of interacting with eNOS and decreasing eNOS-dependent production of NO.

Molecules that interact with eNOS and decrease subsequent production of NO are within the scope of the invention. Interaction of caveolins with eNOS results in decreased production of NO by eNOS, leading to a decreased vasodilatory response in endothelial cells. Molecules which interact with eNOS may therefore be used to down-regulate eNOS function. Down-regulation of eNOS may also be accomplished by the use of polyclonal or monoclonal antibodies or fragments thereof directed against eNOS. In a preferred embodiment, these antibodies will bind at the same domain on eNOS as the caveolin scaffolding domain and are within the claimed invention. This invention further includes small molecules with the three-dimensional structure necessary to bind with sufficient affinity at the same domain on eNOS as the caveolin scaffolding domain (e.g., the oxygenase domain). eNOS blockade resulting in decreased production of NO and decreased vascular permeability during the acute phase of inflammation make these small molecules useful as therapeutic agents in blocking inflammation.

The invention further provides binding agents specific to eNOS, capable of binding at the same domain on eNOS as the caveolin scaffolding domain (e.g., the oxygenase domain), modulating production of NO by altering the activity of eNOS. Such agents include substrates, agonists, antagonists, natural intracellular binding targets, etc. The invention also provides methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins, e.g., eNOS regulation of NO-dependent vasodilation.

Novel binding agents include isolated peptides comprising the caveolin scaffolding domains found in any animal, including, but not limited to, the caveolin scaffolding domains found in rats, dogs and humans. More specifically, novel binding agents include isolated peptides comprising the caveolin-1 scaffolding domains or the caveolin-3 scaffolding domains of any animal. Novel agents also include eNOS-specific receptors or fragments thereof, specific antibodies or T-cell antigen receptors (see Harlow & Lane, (1988) Antibodies-A Laboratory Manual, Cold Spring Harbor Laboratory Press) and other natural intracellular binding agents identified with assays such as one,-two and three-hybrid screens, non-natural intracellular binding agents identified in screens of chemical libraries such as described below, etc. The peptides of the present invention are preferably in isolated form. As used herein, a peptide is said to be isolated when physical, mechanical or chemical methods are employed to remove the protein from cellular constituents that are normally associated with the protein. A skilled artisan can readily employ standard purification methods to obtain an isolated protein.

Agents of particular interest modulate eNOS function, e.g., production of NO. For example, inhibitors of eNOS activity may be used to regulate physiological activity dependent on eNOS such as NO-mediated vasodilation. Exemplary eNOS inhibitors include competitive inhibitors of caveolin binding at the site on eNOS where the caveolin scaffolding domain binds (e.g., the oxygenase domain), for example, the peptides set forth in SEQ ID NO: 1-4 and conservative substitutions thereof.

Accordingly, the invention provides methods for modulating NO production in a cell both in vitro and in vivo comprising the step of modulating eNOS activity. For example, eNOS function may be inhibited by contacting the cell with an agent which binds to eNO, such as a caveolin scaffolding domain Alternatively, eNOS function may be stimulated by contacting the cell with agents which bind to eNOS. Examples of such agents include, but are limited to, calmodulin, heat shock protein-90 and dynamin-2. In addition, the kinase Akt can phosphorylate eNOS on serine 1179 (bovine) or 1177 (human) and lead to an increase in the activity of eNOS. Thus, the present invention includes both agonists and antagonists of eNOS activity. The cells which are utilized may reside in culture or in situ, i.e., within the natural host. Preferred inhibitors and stimulators of eNOS are orally active in animals hosts, more preferably in mammalian hosts, and even more preferably in human hosts. For diagnostic uses, the inhibitors, stimulators or other eNOS binding agents are frequently labeled, such as with biotinylated label or with fluorescent, radioactive, chemiluminescent, or other easily detectable molecules, either conjugated directly to the binding agent or conjugated to a probe specific for the binding agent.

The agents discussed above represent various effective therapeutic compounds in modulating eNOS interactions and thus regulating NO-mediated processes. Applicants have thus provided antagonists and methods of identifying antagonists that are capable of down-regulating eNOS.

B. Screening Assays

In addition, this invention also provides compounds and methods of screening for compounds that block the function, prevent the synthesis or reduce the biologic stability of eNOS and/or other caveolin-binding proteins. Biologic stability is a measure of the time between the synthesis of the molecule and its degradation. For example, the stability of a protein, peptide or peptide mimetic (Kauvar, Nature Biotech. (1996) 14, 709) therapeutic may be shortened by altering its sequence to make it more susceptible to enzymatic degradation.

The present invention also includes methods of screening for agents which deactivate, or act as antagonists of eNOS function and/or the function(s) of other caveolin-binding proteins. Such agents may be useful in the modulation of pathological conditions associated with alterations in eNOS and/or other caveolin-binding protein levels.

Another embodiment of the present invention provides methods for use in isolating and identifying binding partners of proteins of the invention. For example, agents which interact with eNOS and/or other caveolin-binding proteins, thereby blocking NO production by eNOS or blocking the production of other products by other caveolin-binding proteins. In detail, a protein of the invention is mixed with a potential binding partner or an extract or fraction of a cell under conditions that allow the association of potential binding partners with the protein of the invention. After mixing, peptides, polypeptides, proteins or other molecules that have become associated with a protein of the invention are separated from the mixture. The binding partner bound to the protein of the invention can then be removed and further analyzed. To identify and isolate a binding partner, the entire protein, for instance the entire caveolin-1 protein can be used. Alternatively, a fragment of the protein can be used. For example, the caveolin-1 scaffolding domain peptide fragment comprising can be used to block interaction of caveolin-1 with eNOS at the oxygenase domain.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with either eNOS under conditions in which association of the protein with the binding partner can occur. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density-sediment centrifugation can be used.

After removal of non-associated cellular constituents found in the extract, the binding partner can be dissociated from the complex using conventional methods. For example, dissociation can be accomplished by altering the salt concentration or pH of the mixture.

To aid in separating associated binding partner pairs from the mixed extract, the protein of the invention can be immobilized on a solid support. For example, the protein can be attached to a nitrocellulose matrix or acrylic beads. Attachment of the protein to a solid support aids in separating peptide-binding partner pairs from other constituents found in the extract. The identified binding partners can be either a single protein or a complex made up of two or more proteins. Alternatively, binding partners may be identified using a Far-Western assay according to the procedures of Takayama et al., (1997) Methods Mol. Biol. 69, 171-184 or Sauder et al., (1996) J. Gen. Virol. 77, 991-996 or identified through the use of epitope tagged proteins or GST fusion proteins.

Alternatively, the nucleic acid molecules encoding the peptides of the invention can be used in a yeast two-hybrid system. The yeast two-hybrid system has been used to identify other protein partner pairs and can readily be adapted to employ the nucleic acid molecules herein described (see for example, Stratagene Hybrizap two-hybrid system).

Another embodiment of the present invention provides methods for identifying agents that modulate at least one activity of eNOS and/or other caveolin-binding proteins. Such methods or assays may utilize any means of monitoring or detecting the desired activity.

In one format, the relative amounts of a protein of the invention between a cell population that has been exposed to the agent to be tested compared to an un-exposed control cell population may be assayed. In this format, probes such as specific antibodies are used to monitor the differential expression of the protein in the different cell populations. Cell lines or populations are exposed to the agent to be tested under appropriate conditions and time. Cellular lysate may be prepared from the exposed cell line or population and a control, unexposed cell line or population. The cellular lysates are then analyzed with the probe.

Antibody probes are prepared by immunizing suitable mammalian hosts in appropriate immunization protocols using the peptides. Peptides or proteins comprising the caveolin scaffolding domain are of sufficient length, or if desired, as required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co. may be desirable to provide accessibility to the hapten. The hapten peptides can be extended at either the amino or carboxy terminus with a cysteine residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler & Milstein, (1992) Biotechnology 24, 524-526 or modifications which effect immortalization of lymphocytes or spleen cells, as is generally known. The immortalized cell lines secreting the desired antibodies are screened by immunoassay in which the antigen is the peptide hapten, peptide or protein. When the appropriate immortalized cell culture secreting the desired antibody is identified, the cells can be cultured either in vitro or by production in ascites fluid.

The desired monoclonal antibodies may be recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab' of F(ab)$_2$ fragments is often preferable, especially in a therapeutic context, as these fragments are generally less immunogenic than the whole immunoglobulin.

The antibodies or fragments may also be produced, using current technology, by recombinant means. Antibody regions that bind specifically to the desired regions of the protein can also be produced in the context of chimeras with multiple species origin.

Agents that are assayed in the above method can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a non-random basis which takes into account the sequence of the target site and/or its conformation in connection with the agent's action. Agents can be rationally selected or rationally designed by utilizing the peptide sequences that comprises the eNOS domain which interacts with the caveolin scaffolding domain on any caveolin. For example, a rationally selected peptide agent can be a peptide whose amino acid sequence is identical to the amino acid sequence of SEQ ID NO: 1-4 or a peptide with conservative substitutions thereof.

The agents of the present invention can be, as examples, peptides, small molecules, vitamin derivatives, as well as carbohydrates. A skilled artisan can readily recognize that there is no limit as to the structural nature of the agents of the present invention.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

The present invention further provides isolated nucleic acid molecules that encode the peptide having the fusion peptides of the invention and conservative nucleotide substitutions thereof, preferably in isolated form. Conservative nucleotide substitutions include nucleotide substitutions which do not effect the coding for a particular amino acid as most amino acids have more than one codon (see King & Stansfield (1997), A Dictionary of Genetics, Oxford University Press). Conservative nucleotide substitutions therefore also include silent mutations and differential codon usage. For example, the invention includes the nucleic acid encoding the peptide set forth in SEQ ID NO: 1-4, and conservative nucleotide substitutions thereof. The invention also includes nucleic acids encoding the peptides set forth in SEQ ID NO: 1-4 and conservative nucleotide substitutions thereof. Any nucleic acid that encodes the peptides set forth in SEQ ID NO: 1-4 is encompassed in the invention, given the multiple permutations of nucleotide sequences possible which encode these peptides.

As used herein, a nucleic acid molecule is said to be "isolated" when the nucleic acid molecule is substantially separated from contaminant nucleic acid encoding other polypeptides from the source of nucleic acid. Modifications to the primary structure of the nucleic acid itself by deletion, addition, or alteration of the amino acids incorporated into the protein sequence during translation can be made without destroying the activity of the peptide. Such substitutions or other alterations result in peptide having an amino acid sequence encoded by a nucleic acid falling within the contemplated scope of the present invention.

Another class of agents of the present invention are antibodies immunoreactive with critical positions of proteins of the invention. Antibody agents are obtained by immunization of suitable mammalian subjects with peptides, containing as antigenic regions, those portions of the protein intended to be targeted by the antibodies.

C. High Throughput Assays

Introduction—The power of high throughput screening is utilized to the search for new compounds which are capable of interacting with the domains on eNOS or the domains on other caveolin-binding proteins which interact with the caveolin scaffolding domains. For general information on high-throughput screening, see, for example, Devlin, (1996) High Throughput Screening, Marcel Dekker 1998; U.S. Pat. No. 5,763,263. High throughput assays utilize one or more different assay techniques.

Immunodiagnostics and Immunoassays—These are a group of techniques used for the measurement of specific biochemical substances, commonly at low concentrations in complex mixtures such as biological fluids, that depend upon the specificity and high affinity shown by suitably prepared and selected antibodies for their complementary antigens. A substance to be measures must, of necessity, be antigenic—either an immunogenic macromolecule or a haptenic small molecule. To each sample a known, limited amount of specific antibody is added and the fraction of the antigen combining with it, often expressed as the bound:free ratio, is estimated, using as indicator a form of the antigen labeled with radioisotope (radioimmunoassay), fluorescent molecule (fluoroimmunoassay), stable free radical (spin immunoassay), enzyme (enzyme immunoassay), or other readily distinguishable label.

Antibodies can be labeled in various ways, including enzyme-linked immunosorbent assay (ELISA); radioimmuno assay (RIA); fluorescent immunoassay (FIA); chemiluminescent immunoassay (CLIA); and labeling the antibody with colloidal gold particles (immunogold).

Common assay formats include the sandwhich assay, competitive or competition assay, latex agglutination assay, homogeneous assay, microtitre plate format and the microparticle-based assay.

Enzyme-linked immunosorbent assay (ELISA)—ELISA is an immunochemical technique that avoids the hazards of radiochemicals and the expense of fluorescence detection systems. Instead, the assay uses enzymes as indicators. ELISA is a form of quantitative immunoassay based on the use of antibodies (or antigens) that are linked to an insoluble carrier surface, which is then used to "capture" the relevant antigen (or antibody) in the test solution. The antigen-antibody complex is then detected by measuring the activity of an appropriate enzyme that had previously been covalently attached to the antigen (or antibody).

For information on ELISA techniques (see, for example, Crowther, (1995) ELISA: Theory and Practice (Methods in Molecular Biology, Vol. 42), Humana Press; Challacombe & Kemeny, (1998) ELISA and Other Solid Phase Immunoassays: Theoretical and Practical Aspects, John Wiley; Kemeny, (1991) A Practical Guide to ELISA, Pergamon Press; Ishikawa, (1991) Ultrasensitive and Rapid Enzyme Immunoassay (Laboratory Techniques in Biochemistry and Molecular Biology, Vol. 27), Elsevier.

Colorimetric Assays for Enzyme—Colorimetry is any method of quantitative chemical analysis in which the concentration or amount of a compound is determined by comparing the color produced by the reaction of a reagent with both standard and test amounts of the compound, often using a colorimeter. A colorimeter is a device for measuring color intensity or differences in color intensity, either visually or photoelectrically.

Standard colorimetric assays of beta-galactosidase enzymatic activity are well known to those skilled in the art (see, for example, Norton et al., (1985) Mol. Cell. Biol. 5, 281-290). A colorimetric assay can be performed on whole cell lysates using O-nitrophenyl-beta-D-galactopyranoside (ONPG, Sigma) as the substrate in a standard colorimetric beta-galactosidase assay (Sambrook et al., (1989) Molecular Cloning—A Laboratory Manual, Cold Spring Harbor Press). Automated colorimetric assays are also available for the detection of beta-galactosidase activity, as described in U.S. Pat. No. 5,733,720.

Immunofluorescence Assays—Immunofluorescence or immunofluorescence microscopy is a technique in which an antigen or antibody is made fluorescent by conjugation to a fluorescent dye and then allowed to react with the complementary antibody or antigen in a tissue section or smear. The location of the antigen or antibody can then be determined by observing the fluorescence by microscopy under ultraviolet light.

For general information on immunofluorescent techniques, see, for example, Knapp et al., (1978) Immunofluorescence and Related Staining Techniques, Elsevier; Allan, (1999) Protein Localization by Fluorescent Microscopy: A Practical Approach (The Practical Approach Series, Vol. 218) Oxford University Press; Beutner, (1983) Defined Immunofluorescence and Related Cytochemical Methods, New York Academy of Sciences; Caul, (1993) Immunofluorescence Antigen Detection Techniques in Diagnostic Microbiology, Cambridge University Press. For detailed explanations of immunofluorescent techniques applicable to the present invention (see, U.S. Pat. Nos. 5,912,176; 5,869,264; 5,866,319; and 5,861,259).

Biochips—The peptides of the invention can be used on an array or microarray for high-throughput screening for agents which interact with either the nucleic acids of the invention or their corresponding proteins.

An "array" or "microarray" generally refers to a grid system which has each position or probe cell occupied by a defined nucleic acid fragments also known as oligonucleotides. The arrays themselves are sometimes referred to as "chips" or "biochips" which are high-density nucleic acid and peptide microarrays often having thousands of probe cells in a variety of grid styles.

A typical molecular detection chip includes a substrate on which an array of recognition sites, binding sites or hybridization sites are arranged. Each site has a respective molecular receptor which binds or hybridizes with a molecule having a predetermined structure. The solid support substrates which can be used to form surface of the array or chip include organic and inorganic substrates, such as glass, polystyrenes, polyimides, silicon dioxide and silicon nitride. For direct attachment of probes to the electrodes, the electrode surface must be fabricated with materials capable of forming conjugates with the probes.

Once the array is fabricated, a sample solution is applied to the molecular detection chip and molecules in the sample bind or hybridize at one or more sites. The sites at which binding occurs are detected, and one or more molecular structures within the sample are subsequently deduced. Detection of labeled batches is a traditional detection strategy and includes radioisotope, fluorescent and biotin labels, but other options are available, including electronic signal transduction.

The methods of this invention will find particular use wherever high through-put of samples is required. In particular, this invention is useful in ligand screening settings and for determining the composition of complex mixtures.

Polypeptides are an exemplary system for exploring the relationship between structure and function in biology. When the twenty naturally occurring amino acids are condensed into a polymeric molecule they form a wide variety of three-dimensional configurations, each resulting from a particular amino acid sequence and solvent condition. For example, the number of possible polypeptide configurations using the twenty naturally occurring amino acids for a polymer five amino acids long is over three million. Typical proteins are more than one-hundred amino acids in length.

In typical applications, a complex solution containing one or more substances to be characterized contacts a polymer array comprising polypeptides. The polypeptides of the invention can be prepared by classical methods known in the art, for example, by using standard solid phase techniques. The standard methods include exclusive solid phase synthesis, partial solid phase synthesis methods, fragment condensation, classical solution synthesis and recombinant DNA technology (see Merrifield, (1963) Am. Chem. Soc. 85, 2149-2152).

In a preferred embodiment, the polypeptides or proteins of the array can bind to other co-receptors to form a heteroduplex on the array. In yet another embodiment, the polypeptides or proteins of the array can bind to peptides or small molecules.

D. Uses for Agents that Interact with eNOS and/or Other Caveolin-Binding Proteins As provided in the Examples, agents that modulate or up- or down-regulate the expression of eNOS and/or other caveolin-binding proteins or agents such as agonists or antagonists of at least one activity of eNOS and/or other caveolin-binding proteins may be used to modulate biological and pathologic processes (e.g., those associated with the NO-dependent function and activity). In particular, these agents effect NO-mediated processes by interacting with eNOS and can be used to modulate biological or pathological processes associated with NO.

As used herein, a subject can be any mammal, so long as the mammal is in need of modulation of a pathological or biological process mediated by a protein of the invention. The term "mammal" is meant to identify an individual belonging to the class Mammalia. The invention is particularly useful in the treatment of human subjects.

Pathological processes refer to a category of biological processes which produce a deleterious effect. For example, unregulated expression of eNOS is associated with pro-inflammatory processes underlying certain pathological processes. As used herein, an agent is said to modulate a pathological process when the agent reduces the degree or severity of the process. For instance, pro-inflammatory responses may be prevented or pathological processes modulated by the administration of agents which reduce, promote or modulate in some way the expression or at least one activity of eNOS. Agents can therefore be used to treat diseases with a NO-dependent inflammatory component, such disease include but are not limited to; osteoporosis, rheumatoid arthritis, atherosclerosis, asthma (Ray & Cohn, (1999) J. Clin. Invest. 104, 985-993; Christman et al., (2000) Chest 117, 1482-1487) and Alzheimer's disease.

Pathological processes associated with a pro-inflammatory response in which the agents of the invention would be useful for treatment include, but are not limited to, asthma, allergies such as allergic rhinitis, uticaria, anaphylaxis, drug sensitivity, food sensitivity, etc. and the like; cutaneous inflammation such as dermatitis, eczema, psoraisis, contact dermatitis, sunburn, aging, etc. and the like; arthritis such as osteoarthritis, psoriatic arthritis, lupus, spondylarthritis, etc. and the like. These agents also are useful for treating chronic obstruction pulmonary disease and chronic inflammatory bowel disease. The peptides of the present invention can be used to replace corticosteroids in any application in which corticosteroids are used including immunosuppression in transplants and cancer therapy.

The agents of the present invention can be provided alone, or in combination with other agents that modulate a particular pathological process. For example, an agent of the present invention can be administered in combination with one or more anti-inflammatory agents or agents used in the treatment of malignant neoplasms, more commonly referred to as cancer. As used herein, two agents are said to be administered in combination when the two agents are administered simultaneously or are administered independently in a fashion such that the agents will act at the same time.

Agents for treating cancer with which the agents of the present invention may be combined include the more conventional natural products such as paclitaxel (Taxol), the semi-synthetics such as etoposide (VP-16) and many newer, diverse agents such as IL-2 and all-trans-retinoic acid. Other agents useful in the treatment of cancer which may be used in combination with the agents of the present invention include, but are not limited to, ara C, Doxorubicin, 5-fluorouracil, Irinotecan (CPT-11), Tamoxifen, Methotrexate, beta-L-dioxolane-cytidine (OddC), Carboplatin and Cisplatin.

The present invention also includes agents for inhibiting tumor growth, including processes of cellular angiogenesis, proliferation, invasiveness, and metastasis in biological systems. Preferably, the agents are employed to inhibit or reduce cancer cell proliferation, invasiveness, metastasis, or tumor incidence in living animals, such as mammals. The method is also readily adaptable for use in assay systems, e.g., assaying cancer cell growth and properties thereof.

Tumors or neoplasms include new growth of tissue in which the multiplication of cells is uncontrolled and progressive. Some such growths are benign, but others are termed "malignant" leading to death of the organism. Malignant neoplasms or "cancers" are distinguished from benign growths that, in addition to exhibiting aggressive cellular proliferation, invade surrounding tissues and metastasize. Moreover, malignant neoplasms are characterized in that they show a greater loss of differentiation (greater "dedifferentiation") and of their organization relative to one another and their surrounding tissues. This property is also called anaplasia.

Neoplasms treatable by the present invention include all solid tumors, i.e., carcinomas and sarcomas. Carcinomas include those malignant neoplasms derived from epithelial cells which tend to infiltrate (invade) the surrounding tissues and give rise to metastases. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue.

The cancers treatable by means of the present invention occur in mammals. Mammals include, for example, humans, as well as pet animals such as dogs and cats, laboratory animals such as rats and mice, and farm animals such as horses and cows. The treatable cancers include, for example, colon cancer, bladder cancer, breast cancer, melanoma, ovarian carcinoma, prostatic carcinoma or lung cancer, and a variety of other cancers as well. The invention is especially useful in the inhibition of cancer growth in adenocarcinomas, including, for example, those of the prostate, breast, kidney, ovary, testes, and colon. The invention is further useful against melanomas, which derive from the melanocytic system in the skin and other organs.

The agents of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

E. Pharmaceutical Preparations

The invention also includes pharmaceutical compositions comprising the agents of the invention together with a pharmaceutically acceptable carrier. Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers are described in Gennaro et al., (1995) Remington's Pharmaceutical Sciences, Mack Publishing Company. In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil or synthetic fatty acid esters, for example, ethyl oleate or triglycerides. Aqueous injection suspensions may contain substances which increase the viscosity of the suspension include, for example, sodium carboxymethyl cellulose, sorbitol, and dextran. Optionally, the suspension may also contain stabilizers.

Liposomes can also be used to encapsulate a drug for delivery into the cell, in particular, hydrophobic drugs. In one embodiment, the invention provides pharmaceutical compositions comprising a the peptide-liposome complex in a pharmaceutically compatible vehicle or carrier. Liposomes are spherical colloidal structures in which an internal aqueous phase is surrounded by one or more phospholipid bilayers. The use of liposomes as drug delivery systems has been disclosed in U.S. Pat. Nos. 3,993,754; 4,235,871; 4,356,167). The compositions are formulated for, preferably, intravenous administration to a human patient in need of the effective delivery of the agent. These complexes are appropriately sized so that they are distributed throughout the body following intravenous administration. In addition, these liposomes can be modified such that they are uniquely suited for the delivery of a specific drug as described in U.S. Pat. No. 5,785,976.

In another embodiment, the invention relates to therapeutic methods comprising the administration to a patient of a therapeutically effective amount of a pharmaceutical composition comprising a peptide in a liposome complex in a pharmaceutically acceptable vehicle. As set forth in detail herein, treatment of a tumor via the systemic (e.g., intravenous) administration of a liposome complex comprising the AP-Cav peptide is an important embodiment of this aspect of the invention.

In another embodiment, micelles can be prepared by a wide variety of methods using an equally diverse group of compounds for effective delivery of the peptides of the invention. Many forms of polymers have been used to form micelles for effective delivery of peptides. These polymers have generally been block copolymers. Such micelle forming polymeric formulations have generally been designed to behave in a pH independent manner and have comprised nonionic polymers or copolymers (Ropert et al., (1992) Biochem. Biophys. Res. Commun. 187, 379-885; Seki et al., (1984) Macromolecules 17, 1692-1698; Kwon & Kazunori, (1995) Adv. Drug Deliv. Rev. 16, 295-309). In a preferred embodiment, the invention includes methods and compositions for the effective delivery of caveolin peptides by providing a formulation containing micelles that include a caveolin peptide which is released from the micelle following administration.

The pharmaceutical formulations for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

The agents of the present invention can be administered via parenteral, subcutaneous, intravenous, intramuscular, intraperitoneal, transdermal or buccal routes. Alternatively, or concurrently, administration may be by the oral route or by inhalation or lavage, directly to the lungs. The dosage administered will be dependent upon the age, health, and weight of the recipient, kind of concurrent treatment, if any, frequency of treatment, and the nature of the effect desired.

The agents used in the method of treatment of this invention may be administered systemically or topically, depending on such considerations as the condition to be treated, need for site-specific treatment, quantity of drug to be administered and similar considerations.

Topical administration may be used. Any common topical formation such as a solution, suspension, gel, ointment or salve and the like may be employed. Preparation of such topical formulations are well described in the art of pharmaceutical formulations as exemplified, for example, by Remington's Pharmaceutical Sciences. For topical application, these compounds could also be administered as a powder or spray, particularly in aerosol form. The active ingredient may be administered in pharmaceutical compositions adapted for systemic administration. As is known, if a drug is to be administered systemically, it may be confected as a powder, pill, tablet or the like or as a syrup or elixir for oral administration. For intravenous, intraperitoneal or intra-lesional administration, the compound will be prepared as a solution or suspension capable of being administered by injection. In certain cases, it may be useful to formulate these compounds in suppository form or as an extended release formulation for deposit under the skin or intramuscular injection. In a preferred embodiment, the compounds of this invention may be administered by inhalation. For inhalation therapy the compound may be in a solution useful for administration by metered dose inhalers or in a form suitable for a dry powder inhaler.

An effective amount is that amount which will modulate the activity or alter the level of a target protein. A given effective amount will vary from condition to condition and in certain instances may vary with the severity of the condition being treated and the patient's susceptibility to treatment. Accordingly, a given effective amount will be best determined at the time and place through routine experimentation. However, it is anticipated that in the treatment of a tumor in accordance with the present invention, a formulation containing between 0.001 and 5 percent by weight, preferably about 0.01 to 1 percent, will usually constitute a therapeutically effective amount. When administered systemically, an amount between 0.01 and 100 mg/kg body weight per day, but preferably about 0.1 to 10 mg/kg, will effect a therapeutic result in most instances.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice. The compounds of this invention can be utilized in vivo, ordinarily in mammals, preferably in humans.

In still another embodiment, the compounds of the invention may be coupled to chemical moieties, including proteins that alter the functions or regulation of target proteins for therapeutic benefit. These proteins may include in combination other inhibitors of cytokines and growth factors that may offer additional therapeutic benefit in the treatment of disorders associated with inflammation. In addition, the molecules of the invention may also be conjugated through phosphorylation to biotinylate, thioate, acetylate, iodinate using any of the cross-linking reagents well known in the art.

The peptides of the present invention can also be coupled to molecules which enhance the transmembrane transport of peptide across a membrane having biotin or folate receptors that initiate transmembrane transport of receptor bound species. The method takes advantage of (1) the location and multiplicity of biotin and folate receptors on the membrane surfaces of most cells and (2) the associated receptor mediated transmembrane processes. Performance of the method involves formation of a complex between a ligand selected from biotin or other biotin receptor-binding compounds, and/or folic acid or other folate receptor-binding compounds, and the peptide. A cell membrane bearing biotin or folate receptors is contacted with this complex, thereby initiating receptor mediated transmembrane transport of the complex. The complex is allowed to contact the membrane surface bearing the corresponding receptors for a time sufficient to initiate and permit transmembrane transport of the complex. The transmembrane transport of the peptides can be promoted in plant, mammalian, and bacterial cells.

In one embodiment of this invention, the target receptor for the method of the present invention is the biotin receptor. Biotin is a necessary cellular nutrient that has been found to be preferentially bound by biotin receptor proteins associated with cellular membranes. Commercially available reagents are used to form a covalent complex between biotin and polynucleotides, proteins, or other desired exogenous molecules. According to one preferred embodiment of the present invention, a biotinylated peptide is brought into contact with a membrane having associated biotin receptors for a time sufficient to allow binding of the biotin moiety of the complex to a corresponding biotin receptor in the membrane. This binding triggers the initiation of cellular processes that results in transmembrane transport of the complex.

In an alternate but equally preferred embodiment of this invention, folate receptors are targeted to enhance cellular uptake of exogenous molecules. Folate binding receptors are found in most types of cells, and they have been demonstrated to bind and trigger cellular internalization of folates. Thus, folic acid and other art-recognized folate receptor-binding ligands can be chemically bonded to the peptides of the invention using art-recognized coupling techniques to provide a folate receptor-binding complex which is readily endocytosed into living cells. In accordance with this embodiment of the present invention, a folate-peptide complex is brought into contact with a membrane having associated folate receptors for a time sufficient to allow binding of the folate moiety of the complex to a corresponding folate receptor. Folate receptor-binding triggers the initiation of cellular processes that result in transmembrane transport of the complex.

The use of biotin and folate receptors is particularly useful for increasing the internalization efficiency (cellular uptake) of peptides that are normally resistant to cellular internalization. Peptides previously recognized as difficult to move across cell membranes can be internalized by a cell through the use of biotin and folate receptors. For example, blockade of eNOS with a caveolin peptide can be accomplished by coupling the caveolin peptide to either biotin or folates, and contacting the cells with the resulting complex for a time sufficient to promote cellular internalization. The use of biotin and folates complexes to enhance cellular uptake of complexed exogenous molecules has been demonstrated in vivo and in vitro (see U.S. Pat. No. 5,635,382).

F. Molecular Biology, Microbiology and Recombinant DNA Techniques

In accordance with the present invention, as described above or as discussed in the Examples below, there may be employed conventional molecular biology, microbiology and recombinant DNA techniques. Such techniques are explained fully in the literature. See for example, Sambrook et al., (1989) Molecular Cloning—A Laboratory Manual, Cold Spring Harbor Press; Glover, (1985) DNA Cloning: A Practical Approach; Gait, (1984) Oligonucleotide Synthesis; Harlow & Lane, (1988) Antibodies—A Laboratory Manual, Cold Spring Harbor Press; Roe et al., (1996) DNA Isolation and Sequencing: Essential Techniques, John Wiley; and Ausubel et. al., (1995) Current Protocols in Molecular Biology, Greene Publishing.

G. Antisense RNA

Antisense molecules are RNA or single-stranded DNA molecules with nucleotide sequences complementary to a specified mRNA. When a laboratory-prepared antisense molecule is injected into cells containing the normal mRNA transcribed by a gene under study, the antisense molecule can base-pair with the mRNA, preventing translation of the mRNA into protein. The resulting double-stranded RNA or RNA/DNA is digested by enzymes that specifically attach to such molecules. Therefore, a depletion of the mRNA occurs, blocking the translation of the gene product so that antisense molecules find uses in medicine to block the production of deleterious proteins. Methods of producing and utilizing antisense RNA are well known to those of ordinary skill in the art (see, for example, Lichtenstein & Nellen (1997), Antisense Technology: A Practical Approach, Oxford University Press.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences. Such DNA sequences may be incorporated into a wide variety of vectors with suitable RNA polymerase promoters such as T7 or SP6. Alternatively, these cDNA constructs that synthesize antisense RNA in a constitutive or inducible manner and can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2'O-methyl rather than phosphodiesterase linkages within the backbone of the molecule. This concept can be extended by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

H. Fusion Proteins

As it is more generally known, a fusion protein is an expression product resulting from the fusion of two genes. Such a protein may be produced, e.g., in recombinant DNA expression studies or, naturally, in certain viral oncogenes in which the oncogene is fused to gag. As used herein, it more specifically refers to a peptide, polypeptide or protein wherein a peptide comprising a membrane translocation domain is linked to a heterologous peptide The production of a fusion protein sometimes results from the need to place a cloned eukaryotic gene under the control of a bacterial promoter for expression in a bacterial system. Sequences of the bacterial system are then frequently expressed linked to the eukaryotic protein. Fusion proteins are used for the analysis of structure, purification, function, and expression of heterologous gene products.

A fused protein is a hybrid protein molecule which can be produced when a nucleic acid of interest is inserted by recombinant DNA techniques into a recipient plasmid and displaces the stop codon for a plasmid gene. The fused protein begins at the amino end with a portion of the plasmid protein sequence and ends with the protein of interest.

The production of fusion proteins is well known to one skilled in the art (see, e.g., U.S. Pat. Nos. 5,908,756; 5,907,085; 5,906,819; 5,905,146; 5,895,813; 5,891,643; 5,891,628; 5,891,432; 5,889,169; 5,889,150; 5,888,981; 5,888,773; 5,886,150; 5,886,149; 5,885,833; 5,885,803; 5,885,779; 5,885,580; 5,883,124; 5,882,941; 5,882,894; 5,882,864; 5,879,917; 5,879,893; 5,876,972; 5,874,304; and 5,874,290). For a general review of the construction, properties, applications and problems associated with specific types of fusion molecules used in clinical and research medicine, see Chamow et al., (1999) Antibody Fusion Proteins, John Wiley.

I. Peptide Mimetics.

This invention also includes peptide mimetics which mimic the three-dimensional structure of the caveolin scaffolding domain and bind to eNOS. As used herein, a "peptide mimetic" of a known polypeptide refers to a compound that mimics the activity of the peptide or polypeptide, but which is composed of molecules other than, or in addition to, amino acids. Such peptide mimetics may have significant advantages over: naturally-occurring peptides, including, for example, more economical production, greater chemical stability, enhanced pharmacological properties (half-life, absorption, potency, efficacy, etc.), altered specificity (e.g., a broad-spectrum of biological activities), reduced antigenicity, and others.

In one form, mimetics are peptide-containing molecules that mimic elements of protein secondary structure. See, for example, Johnson et al., (1993) Peptide Turn Mimetics in Biotechnology and Pharmacy, Pezzuto et al., (Editors) Chapman & Hall. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

In another form, peptide analogs are commonly used in the pharmaceutical industry as non-peptide drugs with properties analogous to those of the template peptide. These types of non-peptide compounds are also referred to as "peptide mimetics" or "peptidomimetics" (Fauchere, (1986) Adv. Drug Res. 15, 29-69; Veber & Freidinger, (1985) Trends Neurosci. 8, 392-396; and Evans et al., (1987) J. Med. Chem. 30, 1229-1239, which are incorporated herein by reference) and are usually developed with the aid of computerized molecular modeling.

Peptide mimetics that are structurally similar to therapeutically useful peptides may be used to produce an equivalent therapeutic or prophylactic effect. Generally, peptide mimetics are structurally similar to a paradigm polypeptide (i.e., a polypeptide that has a biochemical property or pharmacological activity), such as the caveolin scaffolding domain, but have one or more peptide linkages optionally replaced by a linkage selected from the group consisting of —$CH_2NH$—, —$CH_2S$—, —$CH_2$—$CH_2$—, —CH=CH-(cis and trans), —$COCH_2$—, —$CH(OH)CH_2$—, and —$CH_2SO$—, by methods known in the art and further described in the following references: Weinstein, (1983) Chemistry and Biochemistry of Amino Acids, Peptides and Proteins, Marcel Dekker; Morley, (1980) Trends Pharmacol. Sci. 1, 463-468 (general review); Hudson et al., (1979) Int. J. Pept. Protein Res. 14, 177-185 (—CH$_2$NH—, CH$_2$CH$_2$—); Spatola et al., (1986) Life Sci. 38, 1243-1249 (—CH$_2$—S); Harm, (1982) J. Chem. Soc. Perkin Trans. 1, 307-314 (—CH—CH—, cis and trans); Almquist et al., (1980) J. Med. Chem. 23, 1392-1398 (—COCH$_2$—); Jennings-White et al., (1982) Tetrahedron Lett. 23, 2533 (—COCH$_2$—); U.S. Pat. No. 4,424,207 (—CH(OH)CH$_2$—); Holladay et al., (1983) Tetrahedron Lett. 24, 4401-4404 (—C(OH)CH$_2$—); and Hruby, (1982) Life Sci. 31, 189-199 (—CH$_2$—S—); each of which is incorporated herein by reference.

Labeling of peptide mimetics usually involves covalent attachment of one or more labels, directly or through a spacer (e.g., an amide group), to non-interfering position(s) on the peptide mimetic that are predicted by quantitative structure-activity data and/or molecular modeling. Such non-interfering positions generally are positions that do not form direct contacts with the macromolecules(s) (e.g., are not contact points in caveolin-eNOS complexes) to which the peptide mimetic binds to produce the therapeutic effect. Derivitization (e.g., labeling) of peptide mimetics should not substantially interfere with the desired biological or pharmacological activity of the peptide mimetic.

Caveolin scaffolding domain peptide mimetics can be constructed by structure-based drug design through replacement of amino acids by organic moieties (see, for example, Hughes, (1980) Philos. Trans. R. Soc. Lond. 290, 387-394; Hodgson, (1991) Biotechnol. 9, 19-21; Suckling, (1991) Sci. Prog. 75, 323-359).

The use of peptide mimetics can be enhanced through the use of combinatorial chemistry to create drug libraries. The design of peptide mimetics can be aided by identifying amino acid mutations that increase or decrease binding of caveolin to eNOS. Approaches that can be used include the yeast two hybrid method (see Chien et al., (1991) Proc. Natl. Acad. Sci. USA 88, 9578-9582) and using the phage display method. The two hybrid method detects protein-protein interactions in yeast (Fields et al., (1989) Nature 340, 245-246). The phage display method detects the interaction between an immobilized protein and a protein that is expressed on the surface of phages such as lambda and M13 (Amberg et al., (1993) Strategies 6, 2-4; Hogrefe et al., (1993) Gene 128, 119-126). These methods allow positive and negative selection for protein-protein interactions and the identification of the sequences that determine these interactions.

For general information on peptide synthesis and peptide mimetics, see, for example, Jones, (1992) Amino Acid and Peptide Synthesis, Oxford University Press; Jung, (1997) Combinatorial Peptide and Nonpeptide Libraries: A Handbook, John Wiley; and Bodanszky et al., (1993) Peptide Chemistry: A Practical Textbook, 2nd Revised Edition, Springer Verlag each of which is hereby incorporated in its entirety.

J. Transgenic Animals

Transgenic animals are genetically modified animals into which recombinant, exogenous or cloned genetic material has been experimentally transferred. Such genetic material is often referred to as a transgene. The nucleic acid sequence of the transgene may be integrated either at a locus of a genome where that particular nucleic acid sequence is not otherwise normally found or at the normal locus for the transgene. The transgene may consist of nucleic acid sequences derived from the genome of the same species or of a different species than the species of the target animal.

The term "germ cell line transgenic animal" refers to a transgenic animal in which the genetic alteration or genetic information was introduced into a germ line cell, thereby conferring the ability of the transgenic animal to transfer the genetic information to offspring. If such offspring in fact possess some or all of that alteration or genetic information, then they too are transgenic animals.

The alteration or genetic information may be foreign to the species of animal to which the recipient belongs, foreign only to the particular individual recipient, or may be genetic information already possessed by the recipient. In the last case, the altered or introduced gene may be expressed differently than the native gene.

Transgenic animals can be produced by a variety of different methods including transfection, electroporation, microinjection, gene targeting in embryonic stem cells and recombinant viral and retroviral infection (see, e.g., U.S. Pat. No. 4,736,866; U.S. Pat. No. 5,602,307; Mullins et al., (1993) Hypertension 22, 630-633; Brenin et al., (1997) Surg. Oncol. 6, 99-1 10; Tuan, (1997) Recombinant Gene Expression Protocols, Methods in Molecular Biology No. 62, Humana Press).

A number of recombinant or transgenic mice have been produced, including those which express an activated oncogene sequence (U.S. Pat. No. 4,736,866); express simian SV40 T-antigen (U.S. Pat. No. 5,728,915); lack the expression of interferon regulatory factor 1 (IRF-1) (U.S. Pat. No. 5,731,490); exhibit dopaminergic dysfunction (U.S. Pat. No. 5,723,719); express at least one human gene which participates in blood pressure control (U.S. Pat. No. 5,731,489); display greater similarity to the conditions existing in naturally occurring Alzheimer's disease (U.S. Pat. No. 5,720,936); have a reduced capacity to mediate cellular adhesion (U.S. Pat. No. 5,602,307); possess a bovine growth hormone gene (Clutter et al., (1996) Genetics 143, 1753-1760) or, are capable of generating a fully human antibody response (Zou et al., (1993) Science 262, 1271-1274).

While mice and rats remain the animals of choice for most transgenic experimentation, in some instances it is preferable or even necessary to use alternative animal species. Transgenic procedures have been successfully utilized in a variety of non-murine animals, including sheep, goats, pigs, dogs, cats, monkeys, chimpanzees, hamsters, rabbits, cows and guinea pigs (see Kim et al., (1997) Mol. Reprod. Dev. 46, 515-526; Houdebine, (1995) Reprod. Nutr. Dev. 35, 609-617; Petters, (1994) Reprod. Fertil. Dev. 6, 643-645; Schnieke et al., (1997) Science 278; 2130-2133; Amoah, (1997) J. Animal Science 75, 578-585).

The method of introduction of nucleic acid fragments into recombination competent mammalian cells can be by any method which favors co-transformation of multiple nucleic acid molecules. Detailed procedures for producing transgenic animals are readily available to one skilled in the art, including the disclosures in U.S. Pat. Nos. 5,489,743 and 5,602,307.

The present invention comprises transgenic animals expressing a gene encoding the caveolin scaffolding domain fusion protein (AP-Cav), and mutations of that gene resulting in conservative and non-conservative amino acid substitutions when compared to the wild type gene.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

Example 1

Caveolin-1 Scaffolding Domain Fusion Peptides

Peptides, corresponding to the putative scaffolding domain of human caveolin-1 (SEQ ID NO: 1) or the scrambled control peptide Cav-X (WGIDKAFFTTSTVTYKWFRY) (SEQ ID NO: 9) fused to the antennapedia internalization sequence (RQIKIWFQNRRMKWKK) (SEQ ID NO: 10) were synthesized to form a Caveolin-1 scaffolding domain—antennapedia fusion peptide (AP-Cav; SEQ ID NO: 11 or AP-Cav-X; SEQ ID NO: 12). Peptides were synthesized by standard F-moc chemistry, purified and analyzed by reverse phase HPLC and mass spectrometry by the W. M. Keck Biotechnology Resource center at Yale University School of Medicine. For tissue or cellular internalization studies, peptides were synthesized with an aminohexanoic acid spacer followed by biotin or rhodamine at the amino termini.

Example 2

AP-Cav Inhibits Endothelium-dependent Relaxations of Isolated Blood Vessels For isolated mouse aortic rings preparations, male C57 black mice (5-7 weeks of age) were anesthetized with methoxyflurane and sacrificed by exsanguination. The thoracic aorta was dissected and cut into cylindrical segments of three millimeters in length. Using a sterile 48-well tissue culture plate, each ring was incubated in a total volume of one ml with either peptides or vehicle (DMSO) diluted in DMEM supplemented with penicillin (100 units/ml), streptomycin (100 µg/ml) and L-glutamine (1 mM). The plate was incubated with 5% $CO_2$. Following incubation with the peptides (one, six, twelve or twenty hours), rings were washed in oxygenated (95% $O_2$-5% $CO_2$) Krebs-Henseleit bicarbonate buffer solution (KITS) of the following composition (NaCl-118.3 mmol/L, KCl-4.7 mmol/L, $CaCl_2$-2.5 mmol/L, $MgSO_4$-1.2 mmol/L, $KH_2PO_4$-1.2 mmol/L; $NaHCO_3$-25 mmol/L, glucose-5.6 mmol/L at 37° C. with ibuprofen (10 µM). The rings were suspended by two tungsten wires (25 mm thickness) inserted into the lumen and mounted in a vessel myograph system (five ml chamber, Kent Scientific). The mouse aortas were submitted to a resting tension of 1.5 grams and isometric tension was recorded using a force transducer coupled to a MacLab data acquisition system. Following a sixty minute equilibration period, with frequent washes, the rings were precontracted with phenylephrine (PE) (10 µM; sub maximal concentration) and concentrations of Ach (1 nM-10 µM), sodium nitroprusside (10 µM) or Nitro-L-Arginine Methyl Ester (L-NAME, 100 mM) were injected at the plateau of the PE contraction. In some experiments concentration-response curves to the contractile effects of PE were monitored.

Figure 6:
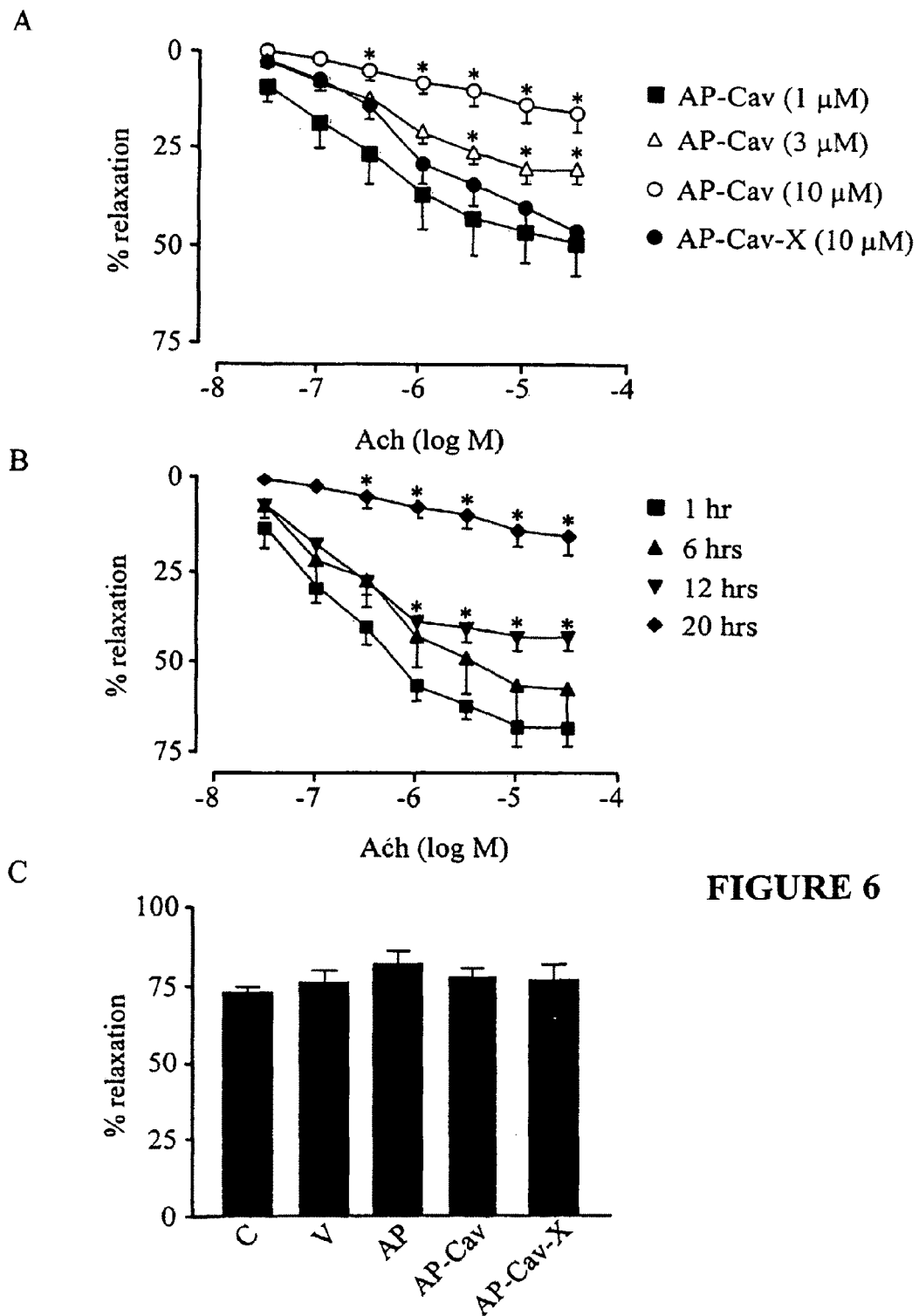
FIG. 6—Concentration-dependent inhibition of acetylcholine-induced relaxation by caveolin scaffolding domain peptide in the isolated mouse aorta. (A) isolated blood vessel were incubated for twenty hours in presence of AP-Cav (1, 3, 10 µM) or AP-Cav-X (10 µM) (*p<0.05 vs AP-Cav-X, n=6-8 rings per treatment). (B) time-dependent effects of AP-Cav peptides on acetylcholine-induced relaxation of isolated mouse aortas. Blood vessels were incubated for one, six, twelve and twenty hours with AP-Cav peptides (10 µM) and following a phenylephrine (PE) precontraction the vessels were then subjected to increasing concentration of acetylcholine (Ach) (30 nM to 30 µM expressed as Log of molar concentration) (*p<0.05 vs control, n=6-8 rings per time point). (C) caveolin peptides do not affect the endothelium independent vascular relaxation of mouse aortas. Sodium nitroprusside (10 µM) induced relaxation of PE precontracted blood vessel was assessed in either control isolated mouse aortas or following a twenty hours incubation of the vessels with vehicle (V), antennapedia alone (AP; 30 µM), AP-Cav (10 µM) or AP-Cav-X (10 µM) (n=6-8 rings per treatment).

To examine the importance of caveolin as a negative regulator of eNOS in intact blood vessels, the primary eNOS binding domain of caveolin-1 (the scaffolding domain; amino acids 82-101) was synthesized as a carboxy terminal fusion protein with the homeodomain of Antennapedia (AP), a Drosophila transcription factor (AP-Cav). The AP protein facilitates the homogeneous uptake of peptides or oligonucleotides into cultured mammalian cells through a non-endocytic, non-degradative pathway (Derossi et al., (1998) Trends Cell Biol. 8, 84-87; Derossi et al., (1996) J. Biol. Chem. 271, 18188-18193; Derossi et al., (1994) J. Biol. Chem. 269, 10444-10450). As seen in FIG. 1A, incubation of mouse aortic rings with AP-Cav (10 µM) attenuated the ability of acetylcholine (Ach), an endothelium-dependent vasodilator, to elicit relaxation of the blood vessel (trace in left panel). However, incubation of aortic rings with a scrambled version (AP-Cav-X; 10 µM; FIG. 1B trace in right panel) or AP alone (30 µM) did not influence Ach-induced relaxation of the blood vessel. This bioassay data is summarized in FIG. 1C. The inhibitory effects of AP-Cav on Ach-induced relaxations were dose-dependent (1-10 µM) and time-dependent (see FIG. 6). Consistent with the ability of AP-Cav to inhibit eNOS derived NO, preincubation of mouse aorta with AP-Cav, but not AP-Cav-X resulted in potentiation of the vasoconstrictor actions of phenylephrine (PE), an alpha-1 adrenergic receptor agonist (FIG. 1D).

Example 3 eNOS is a Primary Biological Target of AP-Cav in Intact Blood Vessels

Figure 2:
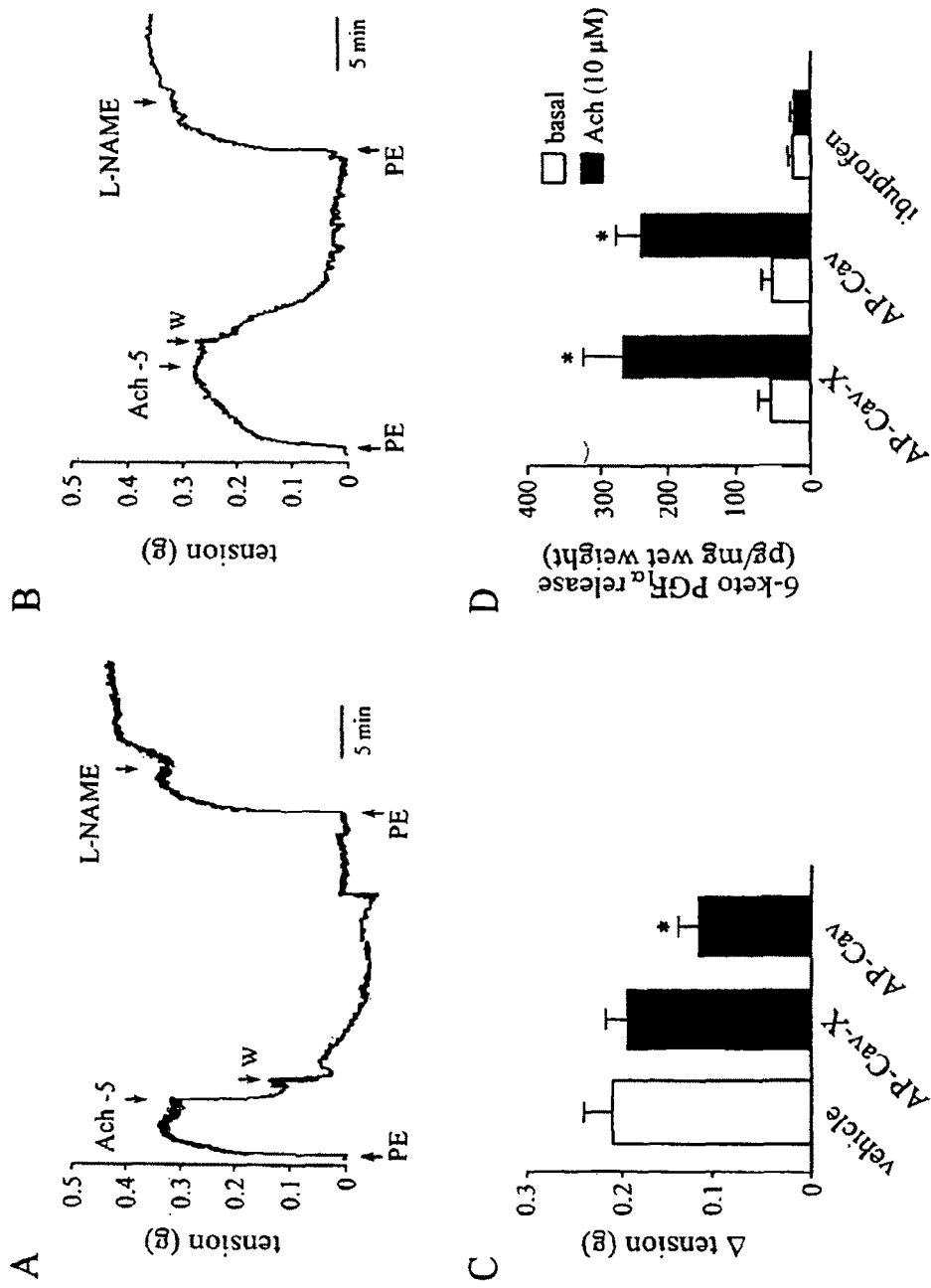
FIG. 2—Evidence that eNOS is a primary biological target of the caveolin scaffolding domain peptide in intact blood vessels. (A-B) show typical recording of L-NAME (100 μM) induced contraction of AP-Cav-X (10 μM) and AP-Cav (10 μM) treated vessels, respectively. Vessels were precontracted with PE to yield similar levels of tone, followed by Ach. Vessels were washed (w), PE preconstricted again, followed by the addition of L-NAME. AP-Cav pretreatment attenuates L-NAME induced contractions of mouse aorta. (C) shows the summary of the further increase in tension elicited by L-NAME in (A) and (B). (D) shows that AP-Cav-X and AP-Cav do not affect Ach-induced prostacyclin release from mouse aortic rings. Prostacyclin release was assessed through measurement of the levels of the stable metabolite of prostacyclin, 6-keto-PGF$_{1a}$ by EIA in rings treated with AP-Cav, AP-Cav-X or ibuprofen, before and after Ach stimulation (thirty minutes) of the vessels (*p<0.05 vs basal prostacyclin levels, *p<0.05 compared to vehicle alone, n=5-7 rings per treatment).

To test the hypothesis that the inhibitory actions of AP-Cav were occurring through inhibition of eNOS, the vasoconstrictor actions of nitro-L-arginine methyl ester (L-NAME) was examined in mouse aortic rings previously preincubated with AP-Cav or AP-Cav-X (FIG. 2). In vessels pretreated with AP-Cav X (A; left panel), Ach-induced relaxation of the vessel segments and the addition of L-NAME, an inhibitor of NOS, further increased isometric tension development due a inhibition of basal NO synthesis. This is in contrast to vessels treated with AP-Cav (panel B). Preincubation of the vessel with AP-Cav inhibited Ach-induced relaxation of the vessel (consistent with NOS inhibition) and also diminished the ability of L-NAME to further increase vascular tension. The inability of L-NAME to further increase isometric tension suggests that a primary molecular target of AP-Cav in the intact blood vessel was indeed eNOS (summary data in C). Furthermore, AP-Cav, AP-Cav-X and AP had no effect of the direct vasorelaxant properties of the NO donor drug, sodium nitroprusside (SNP; see FIG. 6).

To further test the specificity of AP-Cav, Ach-induced prostacyclin production was measured. For measurement of prostacyclin release, after twenty hour incubation period, aortic segments (4-5 mm) were placed in sterile 48-well tissue culture plates with 300 µl of KHS at 37° C. for thirty minutes in an incubator. Then aliquots of 100 ml were taken in order to measure the basal release of prostacyclin. Ach (1 µM) was added and the plate was kept in the incubator for an additional thirty minutes. Aliquots were then taken in order to measure the Ach-stimulated release of prostacyclin. This protocol was performed in absence or in presence of ibuprofen (10 µM). The aliquots were frozen and prostacyclin release was measured as the stable breakdown product, 6-keto-$PGF_{1\alpha}$, by EIA (Amersham).

Ach binds to the muscarinic receptors (M1 and M3) on the endothelium and activates a c-src, G-protein dependent increase in cytoplasmic calcium. The increase in calcium will activate calmodulin to stimulate phospholipases C and A2, arachidonic acid release and its subsequent metabolism by cyclooxygenase and prostacyclin synthase to generate prostacyclin (Smith, (1997) Adv. Exp. Med. Biol. 00, 989-1011). Neither AP-Cav-X nor AP-Cav influenced basal or Ach stimulated prostacyclin production (measured as 6-keto-$PGF_{1\alpha}$) from mouse aortic rings indicating that AP-Cav was not interfering with signal transduction mechanisms leading to prostacyclin production whereas ibuprofen, a cyclooxygenase inhibitor, abolished Ach-induced prostacyclin production (FIG. 2D).

The uptake of AP-Cav into the vessel wall was examined next. A biotinylated version of AP-Cav and AP-Cav-X was synthesized. After twenty hours of incubation with the biotinylated peptides (100 µM) or vehicle, rings were placed in a dish and washed twice with PBS (twenty minutes each time) with light shaking, in order to eliminate the excess of biopeptide that could deposit over the tissue. Then the rings were embedded in OCT medium and cross sections (5 µM thickness) were obtained for staining with an avidin-horseradish peroxidase complex and reactivity was detected with 3-amino-9-ethylcarbazole (AEC).

Figure 3:
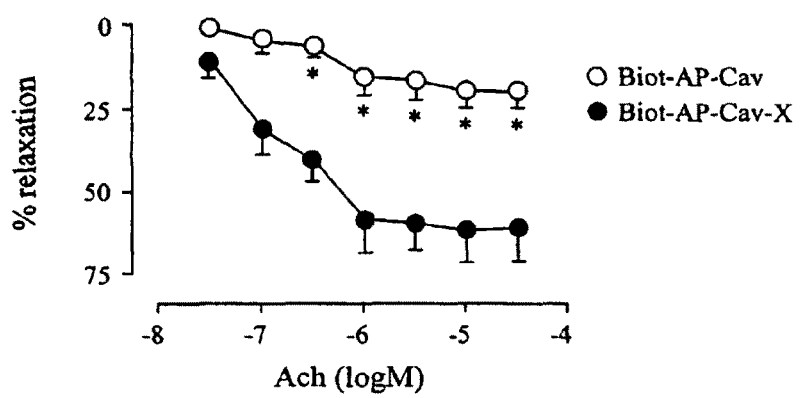
FIG. 3—Biotinylated AP-caveolin peptide inhibits vascular relaxation and localizes to the endothelium and adventitia of mouse aorta. Panel A shows that the biotinylated versions of the AP-Cav-X and AP-Cav peptides (100 mM of each) retained their biological activities. (A) Mouse aortas were incubated with either biotinylated (biot) AP-Cav or biot-AP-Cav-X for twenty hours and subjected to Ach concentration-response curves (*p<0.05 versus biot-AP-Cav-X, n=5 rings per treatment). (B) biot-AP-Cav and biot-AP-Cav-X treated cross sections of mouse aortas stained using HRP-streptavidin (E denotes the endothelium and A denotes adventitia).
Figure 3:
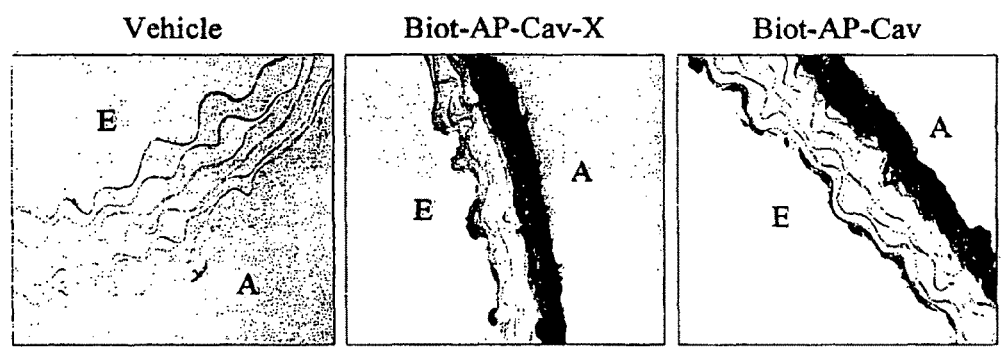

As seen in FIG. 3A, biotinylated AP-Cav (Biot-AP-Cav) but not Biot-AP-Cav-X, inhibited Ach induced relaxation of mouse aorta demonstrating that the biotin conjugate did not interfere with the biological activity of the peptide. Incubation of mouse aorta with Biot-AP peptides resulted in the uptake of both AP-Cav and AP-Cav-X into the endothelium and adventitial lining of the vessel (FIG. 3B). The uptake of both AP-Cav and AP Cav X were identical suggesting that the inhibitory effect of AP-Cav on eNOS was indeed specific. Because the endothelium, but not the cells of the adventitia contain eNOS (Pollock et al., (1993) Am. J. Physiol. 265, C1379-1387) the inhibitory action of AP-Cav is most likely due to inhibition of eNOS in the endothelium. Collectively this data (FIGS. 2 and 3) demonstrates that AP-Cav is selectively inhibiting Ach-induced eNOS dependent vasorelaxation in intact blood vessels.

Example 4

AP-Cav Attenuates No Production from Cultured Endothelial Cells

For measurement of nitric oxide release from cultured endothelial cells, bovine aortic endothelial cells (BAEC) were cultured in high glucose Dulbecco's modified Eagle's medium (DMEM) containing 10% (v/v) fetal bovine serum, penicillin, streptomycin and L-glutamine. For measurement of ionomycin stimulated NO release, confluent BAEC were cultured in C6 well plates. Cells were washed and media was changed to serum free DMEM containing peptides or vehicle (0.01% DMSO). Following a six hour incubation, peptides were washed out and cells were stimulated with ionomycin (1 µM) for thirty minutes. Media was collected and processed for the measurement of nitrite ($NO_2-$), the stable breakdown product of NO in aqueous solution, by NO-specific chemiluminescence. Samples containing $NO_2-$ were refluxed in glacial acetic acid containing sodium iodide. Under these conditions, $NO_2-$ was quantitatively reduced to NO which was quantified by a chemiluminescence detector after reaction with ozone in a NO analyser (Sievers). In all experiments, $NO_2-$ release was inhibitable by a NOS inhibitor.

Ach induced relaxation of the mouse aorta is primarily eNOS mediated since this response is eliminated in eNOS knockout mice (Huang et al., (1995) Nature 377, 239-242). However, to verify that AP-Cav indeed blocked NO release, the uptake and effect of AP-Cav-X and AP-Cav on NO release from cultured aortic endothelial cells was examined using confocal fluorescence microscopy. Briefly, BAEC were grown on gelatin (1%) coated coverslips (50,000 cells/coverslip) and incubated for six hours in presence of labeled peptides (1 µM) in serum free DMEM. Following incubation period, cells were extensively washed and transferred to complete media for sixty minutes before paraformaldehyde (3.5%) fixation. Coverslips were mounted on slides and internalized peptides were visualized using a BioRad MRC 600 confocal microscope.

Figure 4:
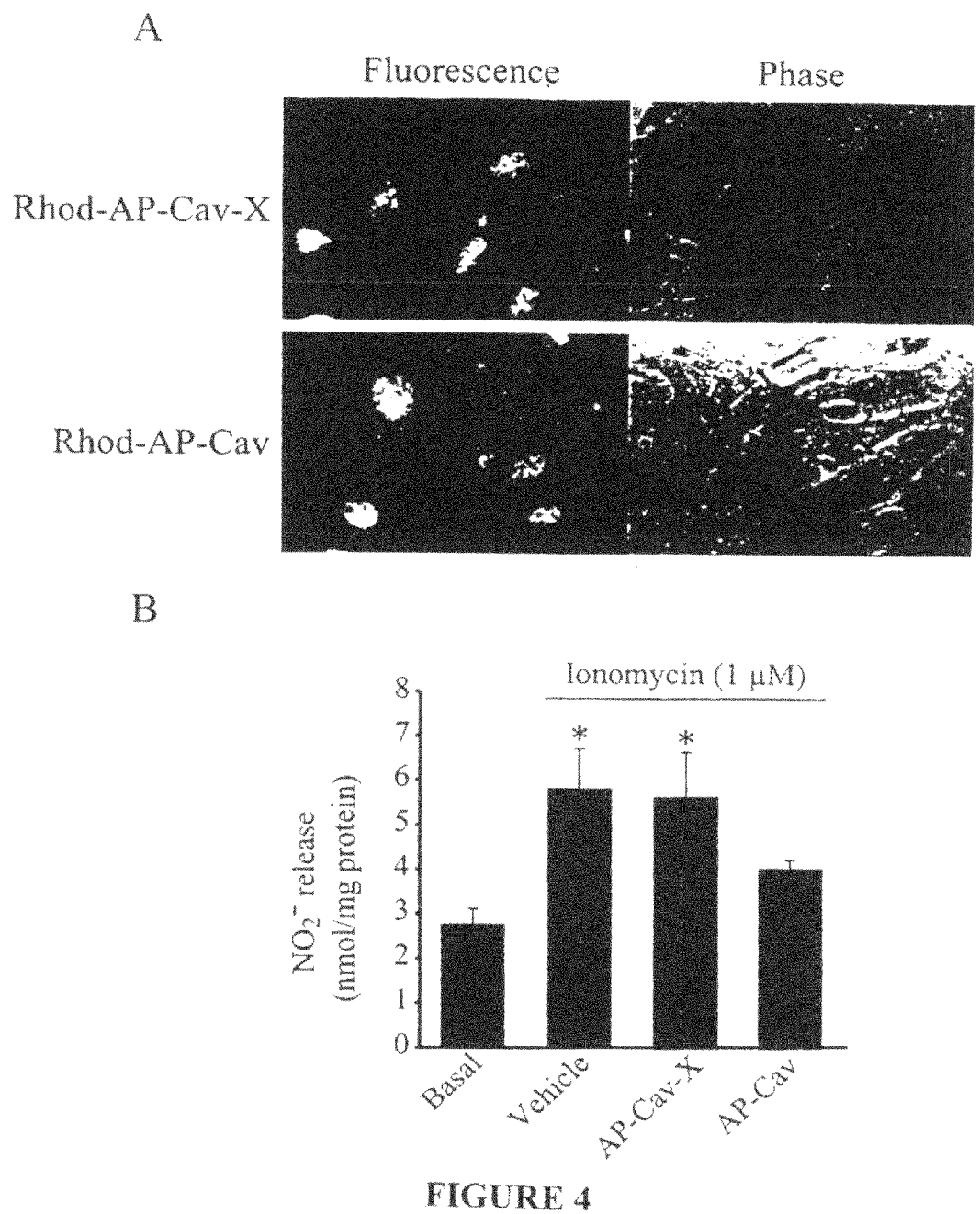
FIG. 4—Cellular uptake and inhibition of nitric oxide release by the AP-caveolin scaffolding domain peptide in cultured endothelial cells. (A) Confocal microscopic imaging of bovine aortic endothelial cells (BAEC) incubated for six hours with either rhodamine labeled AP-Cav-X or AP-Cav (1 µM). Following incubation with the labeled peptides the cells were washed and fixed for fluorescence (left panels) and phase-contrast imaging (right panels). (B) nitric oxide (NO) release from cultured BAEC (measure as levels of nitrate released in the media) incubated for six hours with AP-Cav-X or AP-Cav (1 µM of each). Cells were washed, stimulated with ionomycin (1 µM) and NO release was measured using a NO specific chemiluminescence analyzer (Sievers) (*p<0.05 when compared to basal NO levels, n=5).

As seen in FIG. 4A, incubation of bovine aortic endothelial cells with rhodamine labeled AP-peptides resulted in efficient uptake of the peptide into the cytosol and nucleus. Under these conditions, AP-Cav, but not AP-Cav-X blocked calcium ionophore stimulated NOx release from endothelial cells as quantified by NO specific chemiluminescence. These data in conjunction with results in isolated blood vessels indicates that AP-Cav is an effective inhibitor of eNOS in vivo.

Example 5

AP-Cav Blocks Inflammation in Mice

For in vivo inflammation studies the murine carrageenan induced paw edema model was used. Briefly, male, Swiss mice (25-30 grams) were divided in groups (n=6-7) and lightly anaesthetised with methoxyflurane. Each group of animals received a subplantar administration of 50 µl of 1% (w/v) λ carrageenan. Paw volume was measured using a hydroplethismometer modified for measuring small volumes (Ugo Basile) immediately before the carrageenan injection and twenty-four and forty-eight hours thereafter. The increase in paw volume is evaluated as the difference between paw volume at each time point and the basal volume. AP-Cav (0.3, 1 mg/kg i.p.) AP-Cav-X (1 mg/kg i.p.) and dexamethasone (0.1 mg/kg s.c.) were administered at the time of carrageenin administration (time zero) and at twenty-four and forty-eight hours. In a separate series of experiments, forty-eight hours post carrageenan injections, animals were sacrificed by cervical dislocation and both paws were cut. The right paws were embedded in OCT medium and cross sections (5 µl of thickness) were obtained for staining with hematoxylin and eosin.

Figure 5:
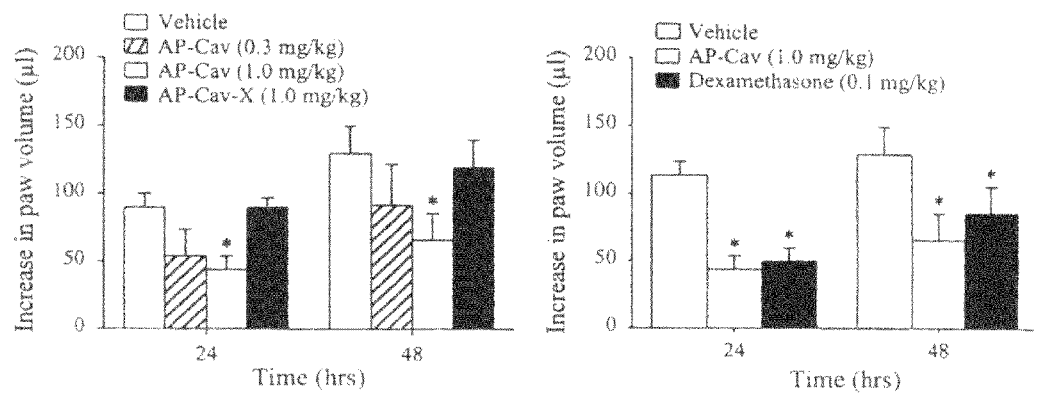
FIG. 5—Caveolin scaffolding domain peptide inhibits carrageenan-induced edema. (A) subplantar injections of 1% carrageenan (50 µl) was injected in both hind paws and the increase in paw volume was monitored at twenty-four and forty-eight hours. AP-Cav-X (0.3 or 1 mg/kg) and AP-Cav (1 mg/kg) were administered intraperitoneal (i.p.) at time zero, twenty-four and forty-eight hours following carrageenin injection (left panel). In a separate experiment, the anti-inflammatory effects of AP-Cav were compared to dexamethasone (0.1 mg/kg; right panel) (*p<0.05 versus vehicle, n=6 mice per group). (B) representative hematoxylin/eosin stained cross sections from control (upper left panel) or carrageenan injected mouse paws 48 hours post-injection. Carrageenan injected mice were treated with either vehicle (upper right panel), AP-Cav-X (1 mg/kg; lower left panel) or AP-Cav (1 mg/kg; lower right panel) as described above. The cross section is oriented with the plantar region of the paw on the right side of each panel. Open arrows show increased cellular infiltration and filled arrows indicates interstitial edema.
Figure 5:
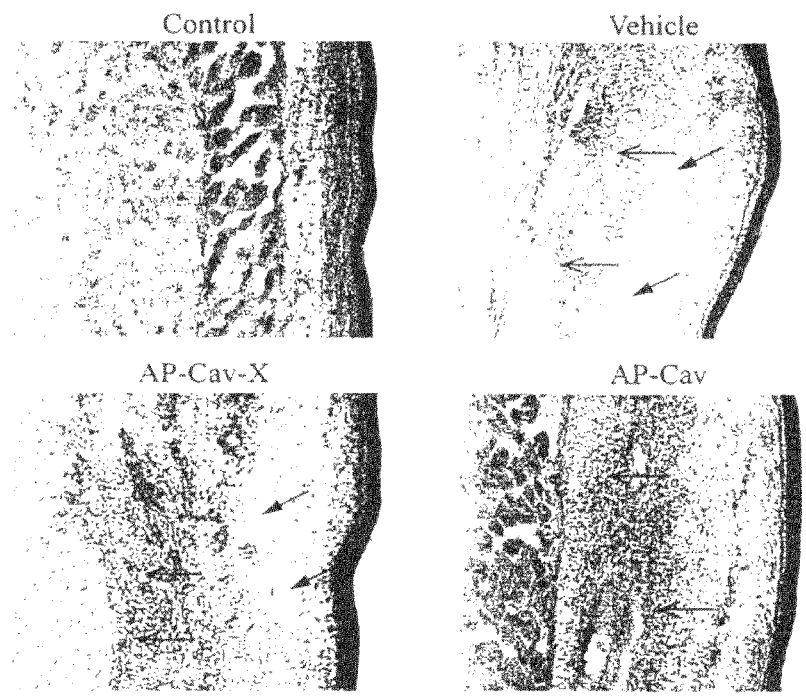

In various models of acute and chronic inflammation, the production of NO has been linked to increase in vascular permeability, edema formation and disease progression. Therefore, we injected mice with carageenan (subplantar) to induce inflammation followed by intraperitoneal administration of vehicle, AP-Cav (0.3 and 1.0 mg/kg) or AP-Cav-X (1.0 mg/kg) at time zero, twenty-four and forty-eight hours. In this model, the first twenty-four hours post-carageenan injection is characterized by edema formation followed by cellular infiltration into the exudate (after twenty-four hours). As seen in FIG. 5A, at twenty-four and forty-eight hours post carrageenan injection, administration of AP-Cav, but not AP-Cav-X, dose-dependently suppressed carrageenan induced edema formation (n=5 mice per group; *p<0.05). Interestingly, the anti-inflammatory efficacy of AP-Cav was comparable to that of the potent anti-inflammatory steroid, dexamethasone (Dex; 0.1 mg/kg administered at zero, twenty-four and forty-eight hours subcutaneously). Histological analysis of carrageenan injected paws demonstrated diffuse inflammation characterized by interstitial edema formation and the presence of inflammatory cells (see control and vehicle treated sections in left and right upper panels). Mice treated with AP-Cav or AP-Cav-X did not show marked differences in the cellular infiltration (bottom left and right panels) into the sites of inflammation. However, AP-Cav treated mice exhibited less interstitial edema (left panel, arrow) consistent with a reduction in paw volume suggesting that the active peptide reduced vascular permeability during inflammation.

Under these conditions when AP-Cav reduced edema formation, AP-Cav did not influence systemic arterial blood pressure or heart rate (89±8, 88±8, and 80±7 mm Hg and 340±27, 280±32 and 320±29 beats per minute for saline, vehicle or AP-Cav treated mice respectively; n=4 mice per group).

These findings underscore the importance of the caveolin scaffolding domain as a regulator of eNOS and perhaps other signaling molecules in vivo. The data provided herein demonstrates that the AP-linked scaffolding domain of caveolin-1 is sufficient to block NO release from intact blood vessels and cultured endothelial cells, while not blocking prostacyclin release. This demonstrates that transduction of the endothelium with the caveolin-1 scaffolding domain does not broadly inhibit all signaling pathways (i.e., c-src dependent calcium fluxes, phospholipases) but selectively targets NOS.

The potent biological activity of the caveolin scaffolding domain peptide in vivo supports the idea that caveolin binding to eNOS via the scaffolding domain can indeed regulate NO production and modulate vascular function.

Example 6

AP-Cav Blocks Tumor Growth

The ability of the AP-Cav peptide to influence tumor growth in vivo was also examined. Nude mice were injected with the HepG-2 cells, a human hepatocarcinoma line, and the effects of AP-Cav and AP-Cav-X examined after daily administration of the peptides intraperitoneal. For HepG-2 cells implants in nude mice, the human hepatocarcinoma cell line, HepG-2, was cultured in minimal essential media with 10% fetal bovine serum, 2 mM L-glutamine, penicillin and streptomycin. Cells were grown on 150 mm dishes up to 80% confluence, trypsinized and ressuspended in serum free media.

Viable cells were counted using the trypan blue exclusion method. A cell suspension was prepared at a density of $5 \times 10^7$ cells/ml. Nude mice were then injected in the flank with 100 µl of the HepG-2 cell suspension.

When the tumors reached a solid palpable mass (7-10 days), treatment with the different drugs began. Peptides were dissolved in 0.01% (v/v) DMSO and administered daily by i.p. injection (100 µl/20 gram mouse) for fourteen days. Tumor volume was determined every day using the formula width$^2$×length×0.52. For histochemistry tumors were excised from the animal at day fourteen, washed in phosphate buffered saline and fixed in 70% ethanol. Tumor tissue was then paraffin imbedded and cross-sections (5 µM) were hematoxylin and eosin stained. Images were captured using a Zeiss microscope coupled to a CCD camera and were recorded with the NIH Image program.

Figure 7:
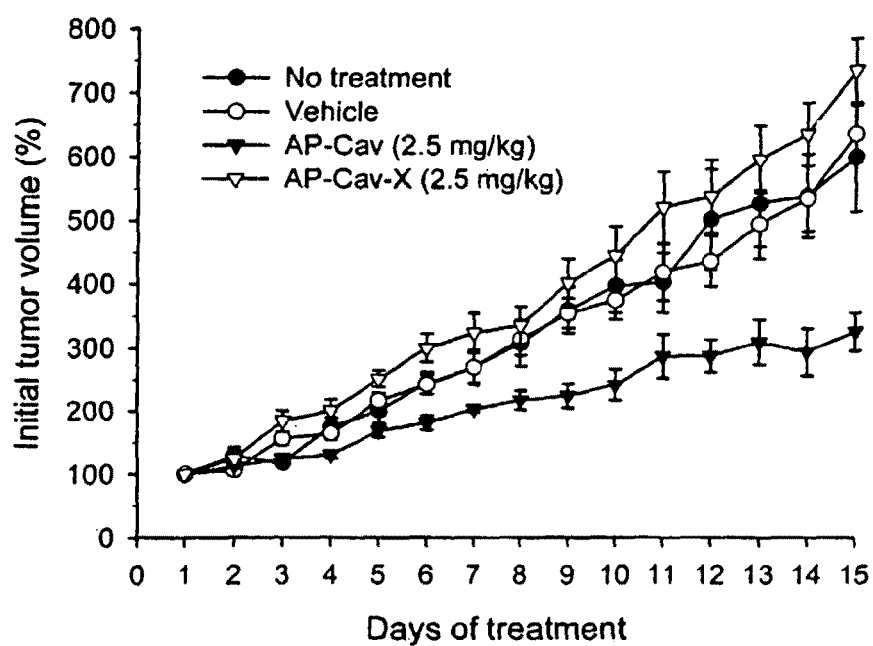
FIG. 7—Reduced tumor burden in Caveolin scaffolding domain peptide treated HepG-2 bearing nude mice. Daily tumor progression of HepG-2 tumors implanted in non treated nude mice or treated with either vehicle, AP-Cav (2.5 mg/kg) or AP-Cav-X (2.5 mg/kg) (*p<0.05 vs AP-Cav-X).
Figure 8:
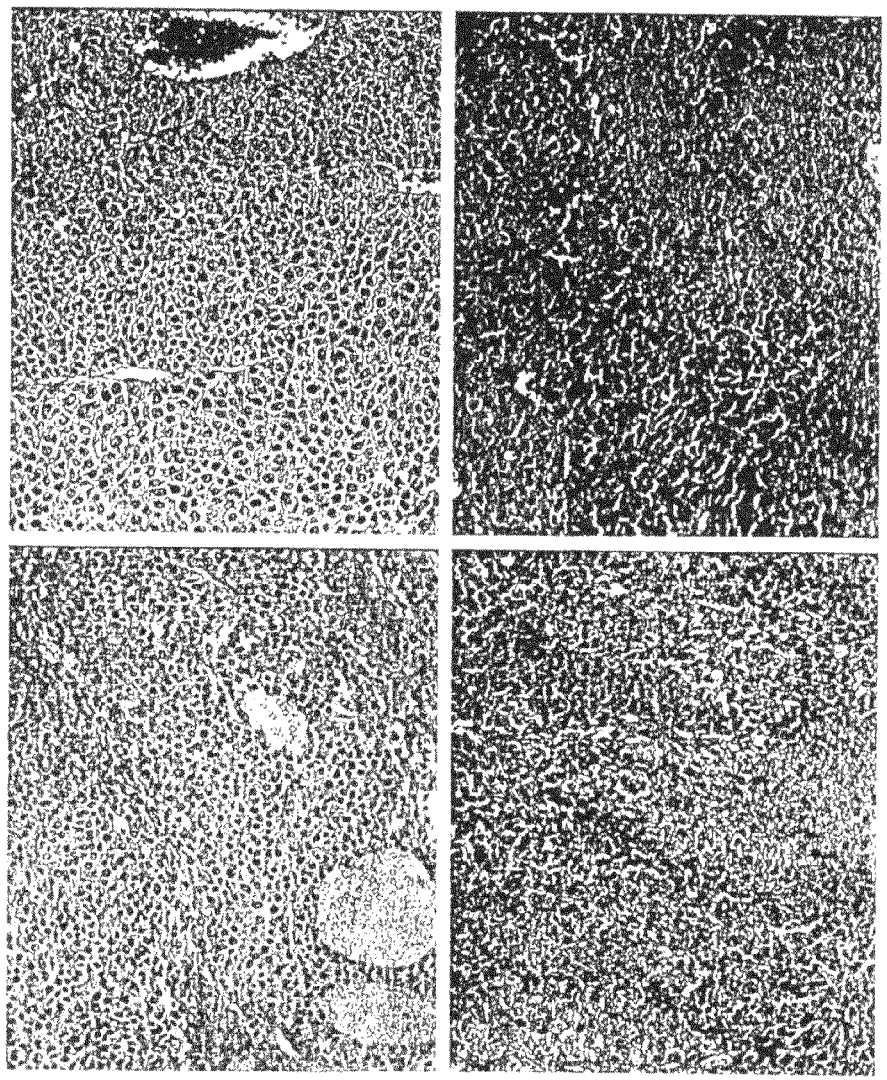
FIG. 8—Disrupted tumor morphology in AP-Cav treated mice. Hematoxylin and eosin staining of HepG-2 tumors at fourteen days of growth in nude mice treated either with AP-Caveolin (2.5 mg/kg; right panel) or AP-Cav-X (2.5 mg/kg; left panel). Pictures are from two different animals (top and bottom).

As seen in FIG. 7, administration of AP-Cav, but not AP-Cav-X significantly reduced the growth of these tumors suggesting that the peptide may interfere with cell division or tumor angiogenesis. Histological staining of tumors revealed that AP-Cav treated mice had unorganized, reduced tumor masses with massive interstitial hemorrhages and few blood vessels, whereas tumors from AP-Cav-X treated mice had a classical epitheliod appearance and were highly vascularized (FIG. 8). Preliminary data demonstrates that the AP-Cav peptide does directly block tumor growth in vitro and that there are few PECAM-1 (an endothelial cell marker) positive endothelial cells in AP-Cav treated mice. This data is consistent with an anti-angiogenic action of the AP-Cav peptide in vivo.

Exampe 7

AP-Cav Attenuates eNOS Dependent NO Production Cells

Ach induced relaxation of the mouse aorta is primarily eNOS mediated since this response is eliminated in eNOS knockout mice. However, to verify that AP-Cav indeed blocked NO release, the uptake and effect of AP-Cav-X and AP-Cav on NO release from cultured aortic endothelial cells was examined.

Figure 9:
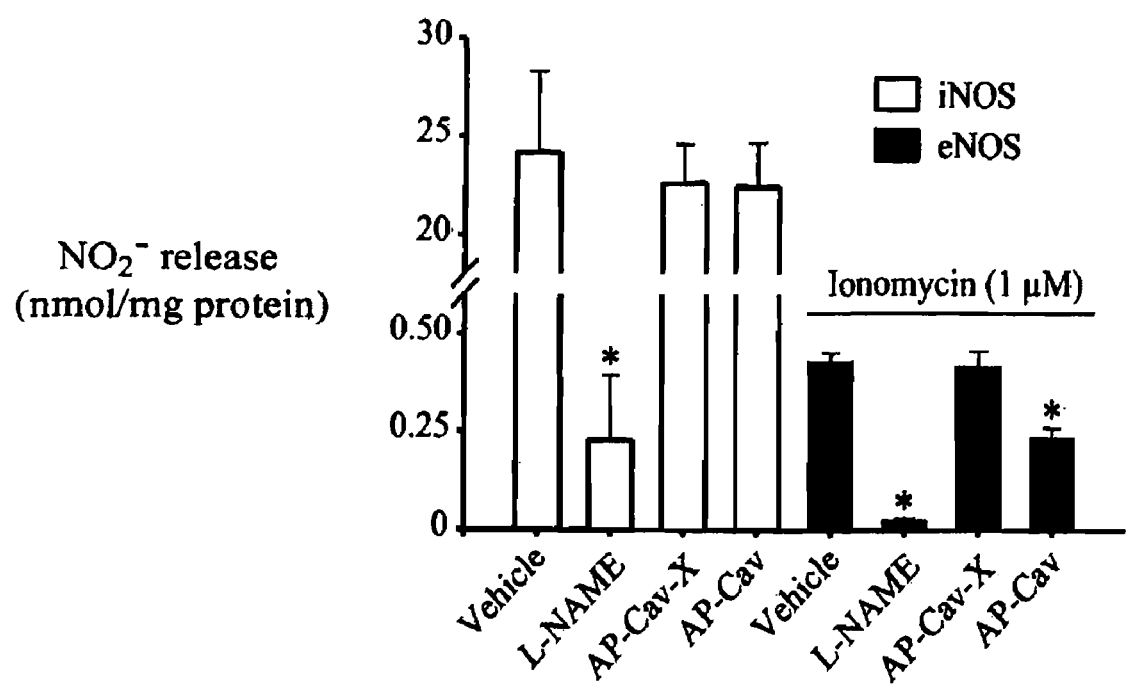
FIG. 9—Cellular uptake and inhibition of nitric oxide release by the AP-caveolin scaffolding domain peptide in cultured endothelial cells and eNOS transfected cells. (A) Confocal microscopic imaging of bovine aortic endothelial cells (BAEC) incubated for six hours with either rhodamine labeled AP-Cav-X or AP-Cav (1 µM). Following incubation with the labeled peptides the cells were washed and fixed for fluorescence (left panels) and phase-contrast imaging (right panels). (B) Nitric oxide (NO) release from cultured BAEC (measure as levels of $NO_2^-$ released in the media) preincubated for six hours with AP-Cav-X or AP-Cav (1 µM of each). Cells were washed, stimulated with ionomycin (1 µM for thirty minutes) and $NO_2$ release was measured using a NO specific chemiluminescence analyzer (Sievers) (*p<0.05 when compared to basal NO levels, n=5). (C) Nitric oxide release from COS-7 cells transfected with iNOS (open bars) or eNOS (closed bars) cDNA. Cells were transfected then treated with either vehicle, AP-Cav, AP-Cav-X for six hours or the arginine analog, L-NAME (1 mM) for thirty minutes and basal $NO_2^-$ accumulation measured for iNOS transfected cells or ionophore induced $NO_2^-$ for eNOS transfected cells. To normalize for $NO_2^-$ background levels, COS cells were transfected with a cDNA for β-galactosidase and the level of $NO_2^-$ in the media subtracted from levels measured in NOS transfected cells. Data are representative of a single experiment in triplicate that was repeated an additional time (*p<0.05 when compared to NO levels from vehicle treated cells).

As seen in FIG. 9A, incubation of bovine aortic endothelial cells with rhodamine labeled AP-peptides resulted in efficient uptake of the peptide into the cytosol and nucleus. Under these conditions, AP-Cav, but not AP-Cav-X blocked calcium ionophore stimulated $NO_x$ release from endothelial cells as quantified by NO specific chemiluminescence (FIG. 9B). To examine if the AP-Cav can also influenced iNOS derived NO production, COS cells were transfected with either the iNOS or eNOS cDNAs and eNO production was examined. As seen in FIG. 9C, transfection of iNOS resulted in marked $NO_2^-$ accumulation, an effect blocked by L-NAME (1 mM), but not by AP-Cav or AP-Cav-X. In contrast, in eNOS transfected cells calcium ionophore stimulated $NO_2^-$ release, an effect blocked by both L-NAME and AP-Cav, but not by AP-Cav-X. These data in conjunction with results in isolated blood vessels indicates that AP-Cav is an inhibitor of eNOS, but not iNOS in intact cells.

Example 8

AP-Cav Reduces Vascular Permeability in Another Model of Inflammation

Figure 10:
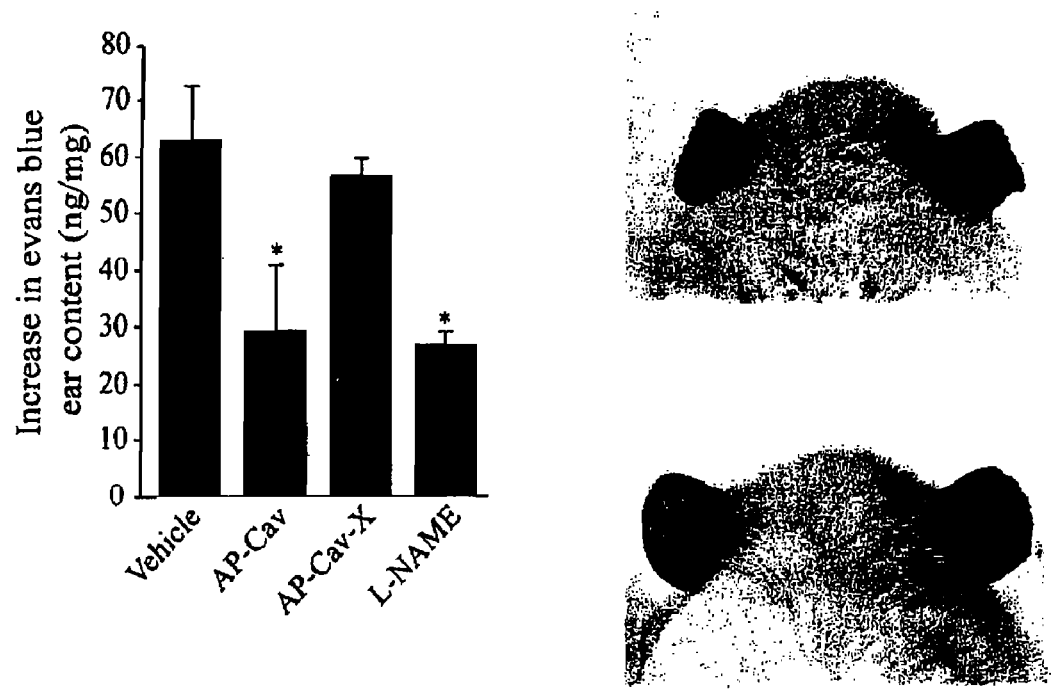
FIG. 10—AP-caveolin peptide reduces vascular leakage. Mice were pretreated with AP-Cav, AP-Cav-X (2 mg/kg of each, i.p.) or L-NAME (30 mg/kg, i.p.) for forty-five minutes followed by Evans blue administration (30 mg/kg, i.v.). Mustard oil was applied to the ventral and dorsal side of the right ear one minute after Evans blue injection. The extent of Evans blue extravasation was assessed after thirty minutes (n=4 mice per group for vehicle and L-NAME treated mice and n=5 for AP-Cav and AP-Cav-X treated mice; *p<0.05). (D) Representative pictures of mice subjected to mustard oil induced inflammation. Note the appearance of dilated vessels and diffuse blue dye in the periphery of the right ear in the lower panel (AP-Cav-X) compared to AP-Cav treated mice (upper panel).

To directly assess if the AP-peptide can influence vascular leakage in an additional model, we treated mice with vehicle, AP-Cav, AP-Cav-X (2 mg/kg, i.p. for each; forty-five minute pretreatment) or L-NAME (30 mg/kg, i.p., thirty-five minute pretreatment) and examined the ability of mustard oil to induce the extravasation of Evans blue, as an index of vascular permeability. Both AP-Cav and L-NAME significantly attenuated vascular leak and overall interstitial edema (FIG. 10C). As illustrated in FIG. 10D, AP-Cav (top panel) reduced the amount of Evans blue in the ear skin and surrounding tissue compared to AP-Cav-X (bottom panel). Thus, in two distinct models, AP-Cav reduces inflammation likely through attenuating eNOS-dependent blood flow and/or permeability changes evoke by inflammatory stimuli.

Although the present invention has been described in detail with reference to examples above, it is understood that various modifications can be made without departing from the spirit of the invention. Accordingly, the invention is limited only by the following claims. All cited patents and publications referred to in this application are herein incorporated by reference in their entirety. The results of the experiments disclosed herein have been published (Bucci et al., (2000) Nat. Med. 6, 1362-1367) after the filing date of U.S. Provisional Application 60/231,327 to which this application claims the benefit of, this publication herein incorporated by reference in its entirety.

The invention claimed is:

1. A fusion peptide comprising at least one caveolin scaffolding domain and at least one membrane translocation domain.

2. The fusion peptide of claim 1 wherein the membrane translocation domain facilitates membrane translocation in vivo.

3. The fusion peptide of claim 1 wherein the membrane translocation domain comprises the third helix of the antennapedia homeodomain.

4. The fusion peptide of claim 1 wherein the caveolin scaffolding domain is selected from the group consisting of SEQ ID NO: 1, SEQ ID NO: 2, SEQ ID NO: 3 and SEQ ID NO: 4.

5. A composition comprising the fusion peptide of claim 1.

6. The composition of claim 5 further comprising a carrier.

* * * * *

UNITED STATES PATENT AND TRADEMARK OFFICE
CERTIFICATE OF CORRECTION

PATENT NO. : 8,349,798 B2  
APPLICATION NO. : 11/978770  
DATED : January 8, 2013  
INVENTOR(S) : William C. Sessa Page 1 of 1

It is certified that error appears in the above-identified patent and that said Letters Patent is hereby corrected as shown below:

In the Specification

Column 1, lines 16-17, please replace the paragraph immediately following the heading, U.S. Government Support, with the following paragraph:

-- This invention was made with government support under HL061371 and HL064793 awarded by National Institutes of Health. The government has certain rights in the invention. --

Signed and Sealed this
Twentieth Day of January, 2015

Michelle K. Lee
*Deputy Director of the United States Patent and Trademark Office*